(12) United States Patent
Schwartz et al.

(10) Patent No.: US 8,042,545 B2
(45) Date of Patent: Oct. 25, 2011

(54) ENDOTRACHEAL INTUBATION AND FLUID DELIVERY DEVICE

(75) Inventors: John Schwartz, Williamston, MI (US); Richard Schwartz, Evans, GA (US)

(73) Assignee: AI Medical Devices, Inc., Williamston, MI (US)

( * ) Notice: Subject to any disclaimer, the term of this patent is extended or adjusted under 35 U.S.C. 154(b) by 861 days.

(21) Appl. No.: 12/148,033

(22) Filed: Apr. 16, 2008

(65) Prior Publication Data

US 2008/0208000 A1  Aug. 28, 2008

Related U.S. Application Data

(63) Continuation of application No. 11/514,486, filed on Sep. 1, 2006, now Pat. No. 7,458,375.

(51) Int. Cl.
*A61M 11/00* (2006.01)
(52) U.S. Cl. .......... 128/207.14; 128/207.15; 128/207.16
(58) Field of Classification Search ............. 128/207.14, 128/207.15, 207.16, 207.17
See application file for complete search history.

(56) References Cited

U.S. PATENT DOCUMENTS

| | | | |
|---|---|---|---|
| 2,975,785 A | 3/1961 | Sheldon | |
| 3,162,214 A | 12/1964 | Bazinet | |
| 4,236,509 A | 12/1980 | Takahashi et al. | |
| 4,669,172 A | 6/1987 | Petruzzi | |
| 4,846,153 A | 7/1989 | Berci | |
| 4,905,666 A | 3/1990 | Fukuda | |
| 4,949,716 A | 8/1990 | Chenoweth | |
| 5,327,881 A | 7/1994 | Greene | |
| 5,520,222 A | 5/1996 | Chikama | |
| 6,539,942 B2 | 4/2003 | Schwartz et al. | |
| 7,556,041 B2 * | 7/2009 | Madsen | 128/207.14 |

FOREIGN PATENT DOCUMENTS

JP   5329095   12/1993

OTHER PUBLICATIONS

U.S. Appl. No. 11/230,392, Apr. 5, 2007, Schwartz, et al.

* cited by examiner

*Primary Examiner* — Steven Douglas
(74) *Attorney, Agent, or Firm* — Ian C McLeod

(57) ABSTRACT

A device for facilitating fluid delivery to the trachea of a patient which comprises, a tubular housing adapted to be sealably mounted on an elongate element of an endoscope for examining the trachea of the patient and configured to mount an adapter for an endotracheal tube for intubating the patient over and around the elongate element, the housing having at least one inlet into a cavity inside the housing for supplying at least a first fluid and an outlet for delivering the first fluid between the elongate element and an inside wall of the endotracheal tube mounted on the adapter.

27 Claims, 19 Drawing Sheets

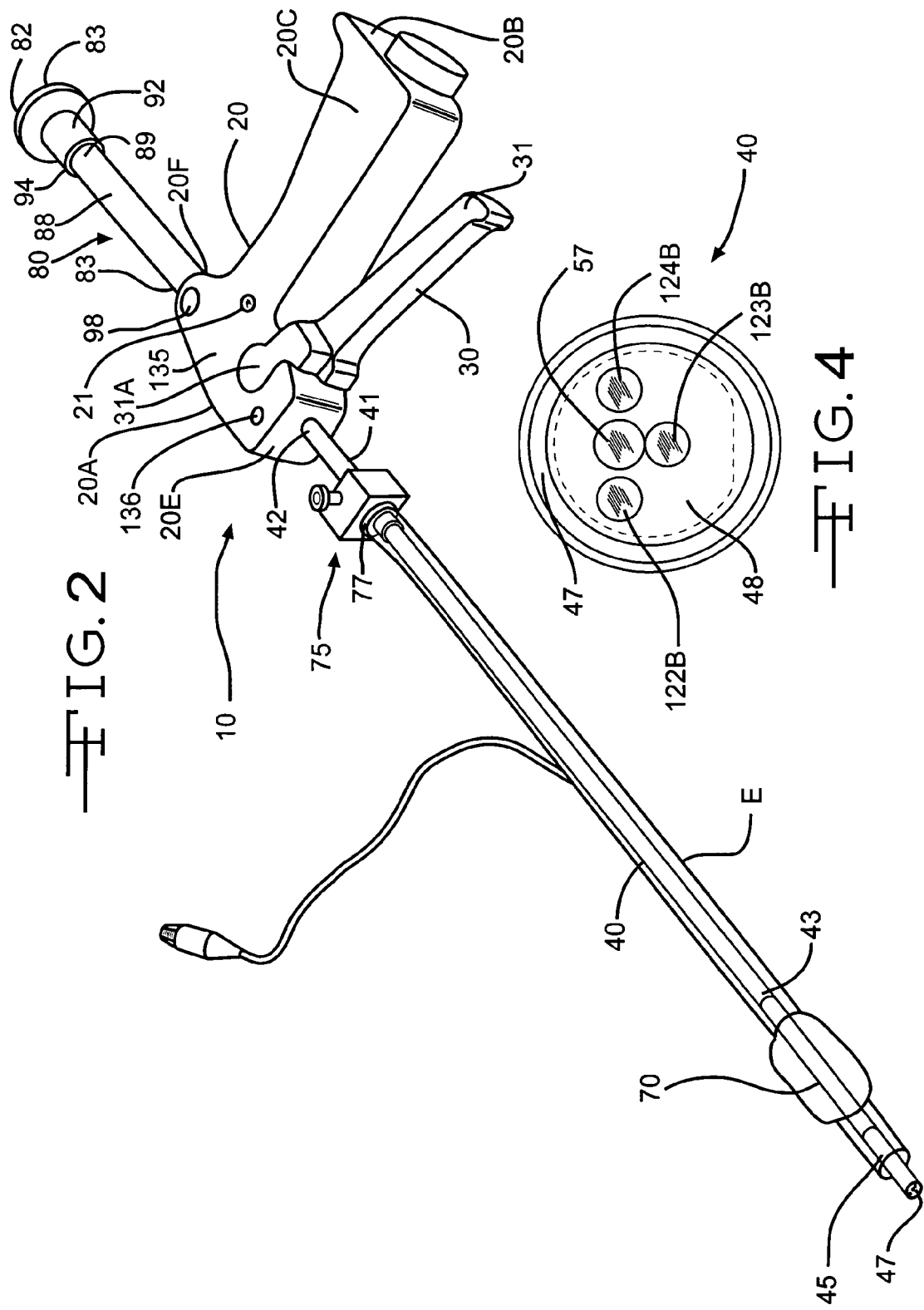

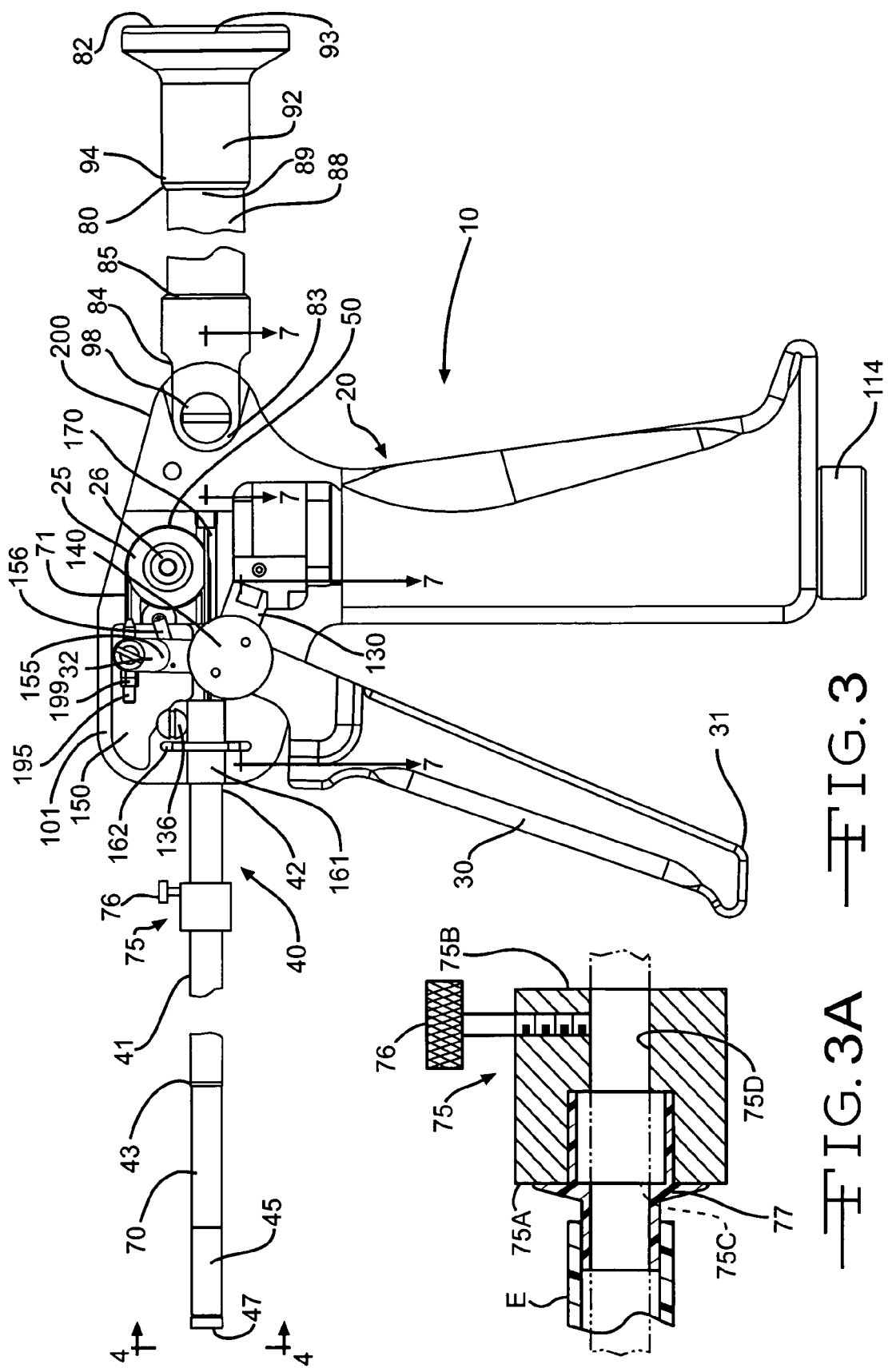

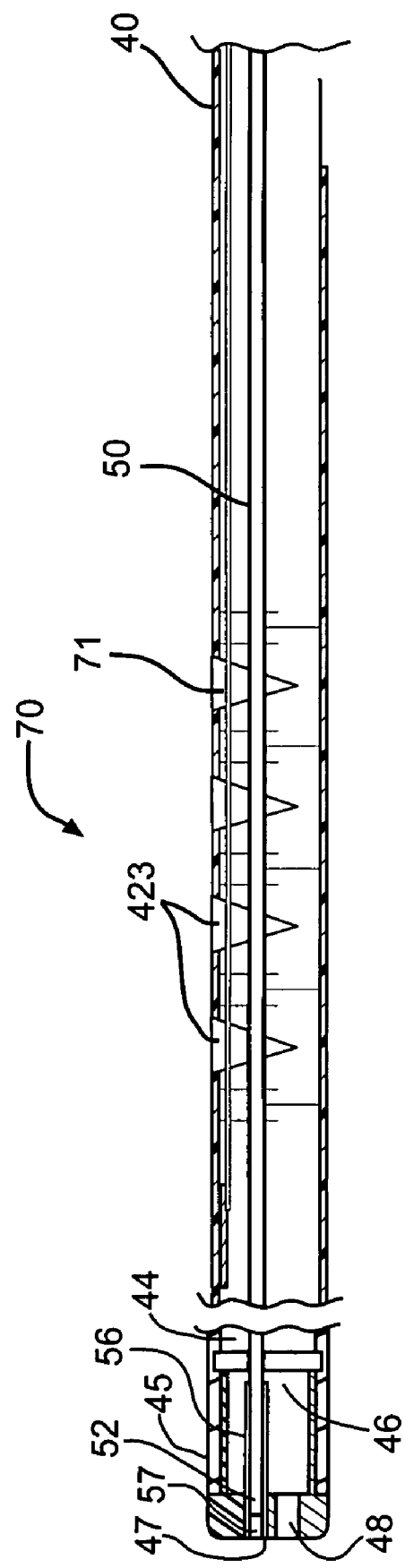

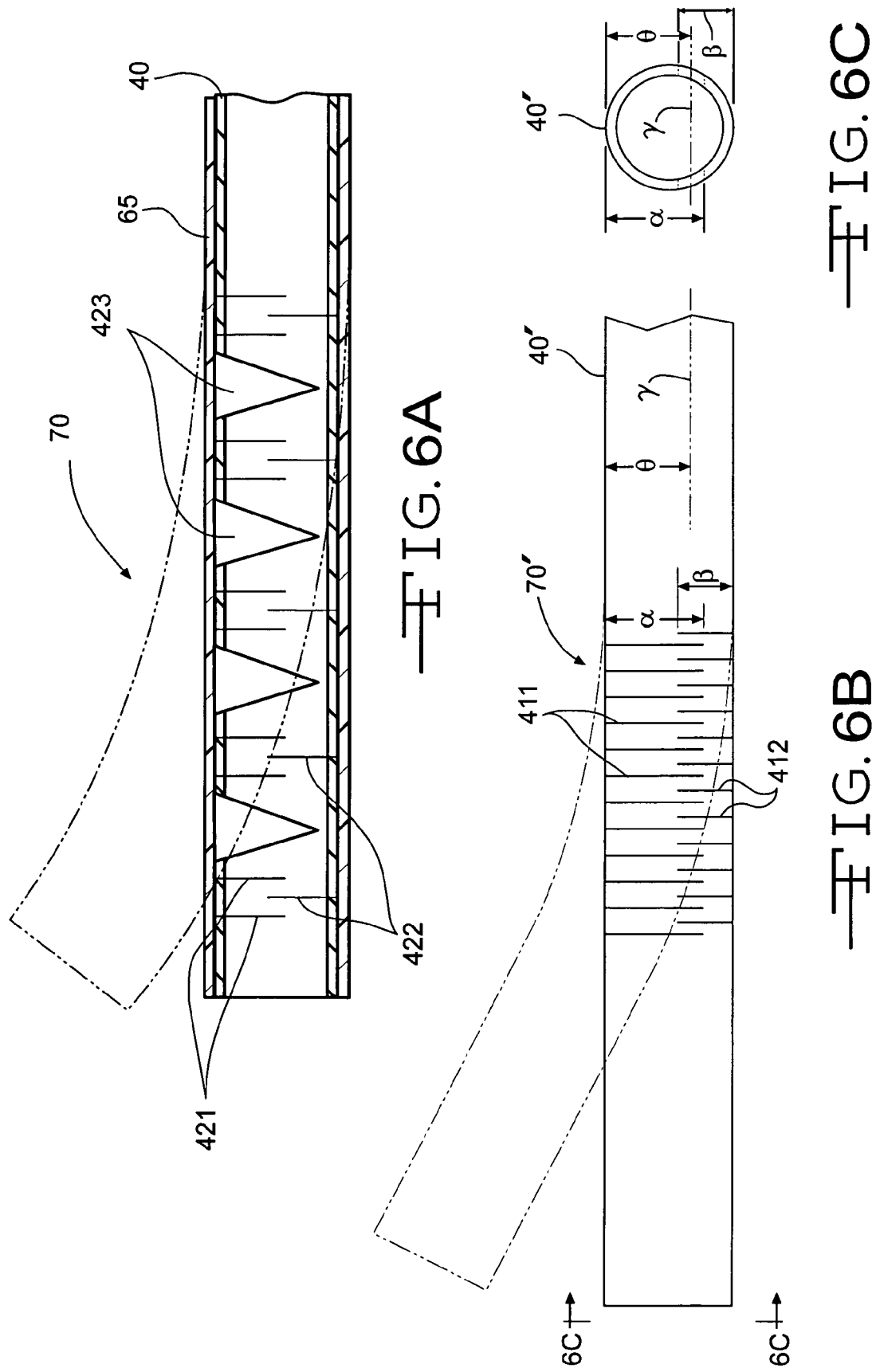

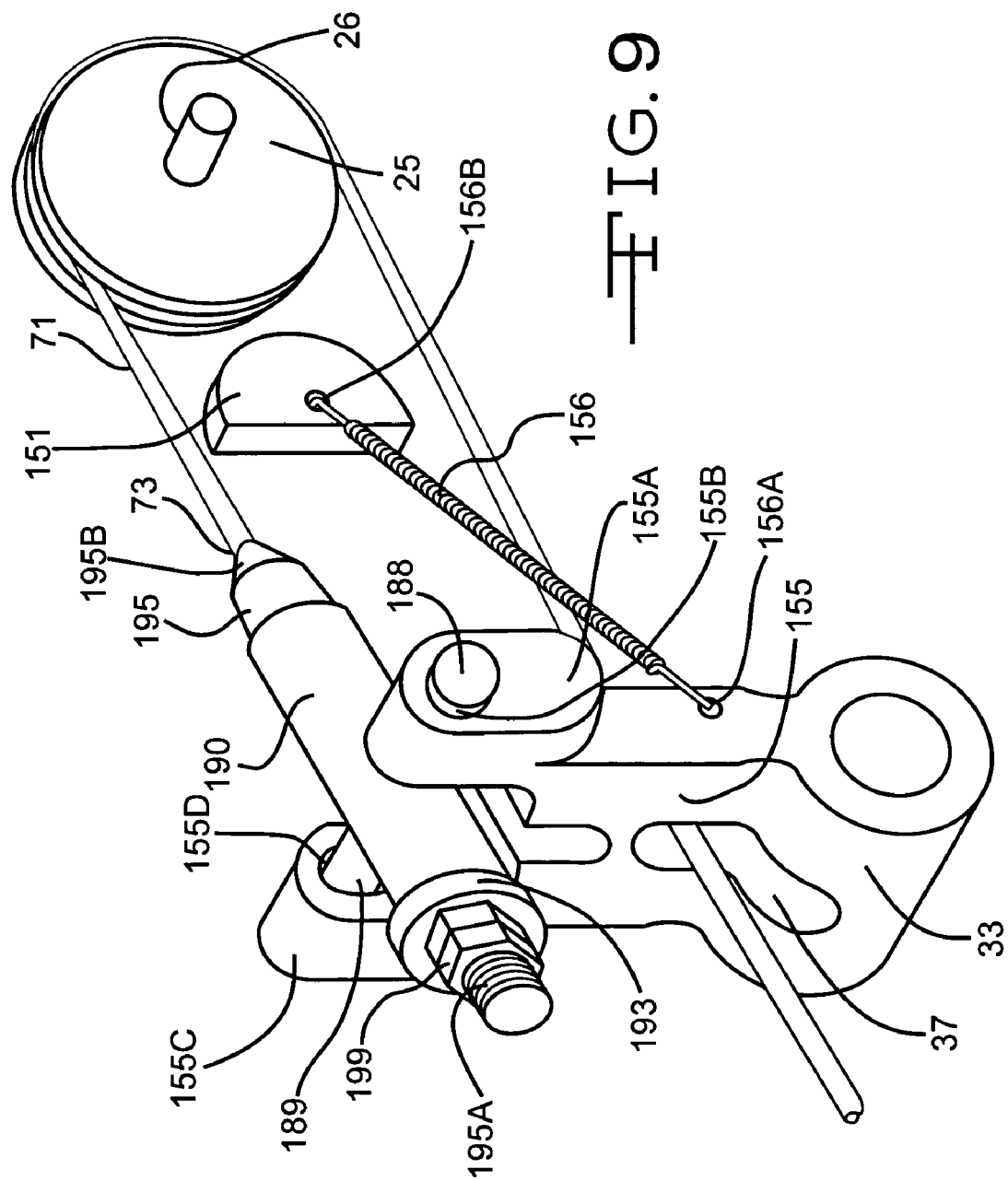

ENDOTRACHEAL INTUBATION AND FLUID DELIVERY DEVICE

CROSS-REFERENCE TO RELATED APPLICATIONS

This application is a continuation-in-part of U.S. application Ser. No. 11/514,486, filed Sep. 1, 2006 now U.S. Pat. No. 7,458,375 which is hereby incorporated in its entirety for all purposes.

STATEMENT REGARDING FEDERALLY SPONSORED RESEARCH OR DEVELOPMENT

Not Applicable.

BACKGROUND OF THE INVENTION (1) Field of the Invention

The present invention relates generally to endotracheal intubation devices, and more specifically to devices for facilitating delivery of a fluid to the trachea of a patient.

(2) Description of the Related Art

U.S. Pat. No. 2,975,785 to Sheldon discloses an optical viewing instrument comprising an endoscope sheath and a plurality of tube elements arranged in an end to end relationship. One end of the sheath is secured to a control housing and has its interior end in communication with the interior chamber of the housing. The control housing serves to support various control structures for the endoscope including cables which are secured to a terminal tube element with the other ends of the cables secured and looped around a pair of pulleys positioned within the chamber. The pulleys are turned by control knobs to flex a terminal section of the endoscope. The instrument has an optical system with a flexible bundle of optically aligned transparent glass fibers. The transparent glass fibers transmit light from an object which is illuminated by a pair of lamps in the end of the instrument so that an image of the object can be seen at an eyepiece.

U.S. patents issued to Bazinet (U.S. Pat. No. 3,162,214), Takahashi et al. (U.S. Pat. No. 4,236,509) and Petruzzi (U.S. Pat. No. 4,669,172) disclose flexible tubular structures composed of coiled wire and/or tethered circular ring elements which provide for flexibility in tubular structures. Petruzzi discloses a method for fabricating a flexible shaft comprising a spiral cut member having an essentially uniform inside diameter and a tapered linear profile.

U.S. Pat. No. 4,846,153 issued to Berci discloses an intubating video endoscope which includes an elongated sheath member with a selectively controllable bendable section housing an image forming optical system. A generally rigid section includes a control housing. An image transmitting optical system extends throughout the length of the sheath member and terminates adjacent to the image forming system. A light transmitting system also extends throughout the length of the sheath member to the image forming optical system, the rearward end of which is adapted to be operatively connected to a light source.

U.S. Pat. No. 4,949,716 issued to Chenoweth discloses a hand held medical device with a wide range of nasally placed airway tubes to afford better control of airway tubes. A soft flexible tube surrounding a flat spring has a braided wire which is pulled to control the flexing of the airway tube.

U.S. Pat. No. 6,539,942 to Schwartz et al., hereby incorporated herein by reference in its entirety, describes an endotracheal intubation device having a series of interlinked, truncated ring-like elements disposed along the distal portion of the tube and a handgrip for controlling the degree of bend in the distal end of the device. An imaging device, such as a nasopharyngoscope, can be inserted through the intubation device to visualize the patient's vocal cords during the intubation procedure. The endotracheal intubation device uses a scissors mechanism without pulleys to bend the distal end of the device.

U.S. Pat. No. 4,905,666 to Fukuda, U.S. Pat. No. 5,520,222 to Chikama, and JP 5,329,095 to Ogino teach bending devices which use pulleys or chain driven winding mechanisms which are controlled by cranks and knobs.

U.S. Pat. No. 5,327,881 to Greene discloses an intubation assisting device having an elongate stylet adapted to fit within a standard endotracheal tube. A flexible bellows region is provided adjacent to the proximal end of the elongate stylet. Flexible optical fibers and illuminating fibers are disposed with the stylet to enable direct viewing by the operator during the intubation process.

While the related art teach endotracheal intubation devices, there still exists a need for an improved device for facilitating delivery of a fluid to the trachea of a patient for use with an endotracheal device.

OBJECTS

Therefore, it is an object of the present invention to provide an improved device for facilitating delivery of a fluid to the trachea of a patient for use with an endotracheal intubation device.

These and other objects will become increasingly apparent by reference to the following description.

SUMMARY OF THE INVENTION

The present invention provides a device to facilitate endotracheal intubation of a patient, comprising: a gripping means; a tubular element having a proximal end attached to the gripping means and a distal end; a curvable portion of the tubular element disposed adjacent to the distal end of the tubular element, having one or more recesses in the tubular element adapted to curve the curvable portion; a control means provided on or adjacent to the gripping means; and a means for moving the curvable portion transmitting force applied by the user on the control means to curve the curvable portion, wherein when the control portion is manipulated by the user the curvable portion curves into a generally curved configuration in a controlled manner from a fully straight configuration and returns to a less curved conformation when the control means is released.

In further embodiments, the tubular element is constructed of stainless steel or a shape memory alloy (SMA). In still further embodiments, the tubular element is constructed of Nitinol. In still further embodiments, the recesses are provided as slits in the curvable portion. In further embodiments, the recesses are provided as wedge shaped cuts in the curvable portion. In still further embodiments, the device further comprises an insufflation attachment to clear secretions from the patient's airway and supply oxygenation. In still further embodiments, the means for moving the curvable portion is a wire attached to the control means. In still further embodiments, wherein the control means is a trigger mounted on the gripping means. In still further embodiments, the device further comprises a display means at a proximal end of the device for displaying of an image of the throat of the patient when the distal end of the tubular element is advanced forward during the endotracheal intubation procedure.

The present invention provides a method of inserting an endotracheal tube into the trachea of a patient comprising: providing a device comprising a gripping means; a tubular element having a proximal end attached to the gripping means and a distal end; a curvable portion of the tubular element disposed adjacent to the distal end of the tubular element, having one or more recesses in the tubular element adapted to curve the curvable portion; a control means provided on or adjacent to the gripping means; and a means for moving the curvable portion transmitting force applied by the user on the control means to curve the curvable portion, wherein when the control portion is manipulated by the user the curvable portion curves into a generally curved configuration in a controlled manner from a fully straight configuration and returns to a less curved conformation when the control means is released; sliding the endotracheal tube over the tubular element of the device; inserting the distal end of the tubular element with the endotracheal tube into the patient's mouth; manipulating the control means to curve the curvable portion enough so that the distal end of the tubular element can be safely advanced in the throat of the patient; advancing the distal end of the tubular element to place the endotracheal tube into the trachea of the patient; and removing the tubular element from the patient's mouth.

In further embodiments, the tubular element is constructed of stainless steel or a shape memory alloy (SMA). In still further embodiments, the tubular element is constructed of Nitinol. In still further embodiments, the recesses are provided as slits in the curvable portion. In further embodiments, the recesses are provided as wedge shaped cuts in the curvable portion. In still further embodiments, the means for moving the curvable portion is a wire attached to the control means. In still further embodiments, the control means is a trigger mounted on the gripping means. In still further embodiments, the control means is manipulated by squeezing.

The present invention provides a method of inserting an endotracheal tube into the trachea of a patient comprising: providing a device comprising a gripping means; a tubular element having a proximal end attached to the gripping means and a distal end; a curvable portion of the tubular element disposed adjacent to the distal end of the tubular element, having one or more recesses in the tubular element adapted to curve the curvable portion; a control means provided on or adjacent to the gripping means; and a means for moving the curvable portion transmitting force applied by the user on the control means to curve the curvable portion, wherein when the control portion is manipulated by the user the curvable portion curves into a generally curved configuration in a controlled manner from a fully straight configuration and returns to a less curved conformation when the control means is released; sliding the endotracheal tube over the tubular element of the device; inserting the distal end of the tubular element with the endotracheal tube into the patient's mouth; viewing the image of the throat of the patient on the display means; manipulating the control means to curve the curvable portion enough so that the distal end of the tubular element can be safely advanced in the throat of the patient; advancing the distal end of the tubular element to place the endotracheal tube into the trachea of the patient; and removing the tubular element from the patient's mouth.

In still further embodiments, the tubular element is constructed of stainless steel or a shape memory alloy (SMA). In still further embodiments, the tubular element is constructed of Nitinol. In still further embodiments, the recesses are provided as slits in the curvable portion. In further embodiments, the recesses are provided as wedge shaped cuts in the curvable portion. In still further embodiments, the means for moving the curvable portion is a wire attached to the control means. In still further embodiments, the control means is a trigger mounted on the gripping means. In still further embodiments, the control means is manipulated by squeezing.

The present disclosure further provides for a device for facilitating fluid delivery to the trachea of a patient, which comprises a tubular housing adapted to be sealably mounted on an elongate element of an endoscope for examining the trachea of the patient and configured to mount an adapter for an endotracheal tube for intubating the patient over and around the elongate element; the housing having at least one inlet into a cavity inside the housing for supplying at least a first fluid and an outlet for delivering the first fluid between the elongate element and an inside wall of the endotracheal tube mounted on the adapter. The housing typically defines a longitudinal axis and comprises: (i) a first portion configured and dimensioned to be mounted along and around the elongate element along the longitudinal axis and is adapted to mount an adapter for the endotracheal tube on a distal end of the housing; and (ii) a second portion integral with the first portion and extending along the longitudinal axis from a proximal end of the first portion, wherein the second portion is adapted at the proximal end of the housing to be mounted on a holding means for securing and sealing an end of the second portion of the elongate element. The inlet extends from an outside surface of the first portion into the cavity and the outlet extends from the cavity defined in the inside of the first portion. The housing is adapted to support a removable adapter mounted on the first portion extending along the longitudinal axis at the distal end of the housing adapted to allow for the endotracheal tube to be sealably mounted along and around the elongate element along the longitudinal axis.

In an exemplary embodiment, the adapter defines an opening extending from a first section to a second section, wherein the opening is sized and shaped to allow the adapter to be mounted along and around the elongate element. The second section is sized and shaped to allow the adapter to be sealably and removably mounted within an opening in the first portion of the housing. In a further embodiment, the adapter comprises an outwardly extending flange member around an outer surface of the adapter to allow a friction fit to form between the adapter and the first portion of the housing. In a still further embodiment, the holding means is an endotracheal tube stop mounted on a proximal end of the tubular element and adapted to form a seal between the second portion and the elongate element. The second portion can be tapered to allow for a friction fit to form between the second portion and the stop.

In an exemplary embodiment, the at least a first inlet is a port connected to a fluid delivery tube for supplying the fluid to the housing. The fluid delivery tube can be fabricated from any suitable material such as a plastic material. In a still further embodiment, the housing can be fabricated from a plastic material and be made disposable after use with a single patient.

In an exemplary embodiment, the device of the present disclosure comprises a second inlet into the cavity of the housing adapted to allow for introducing a second fluid through the outlet to reach the trachea of a patient. In a further embodiment, the second inlet comprises a luer-lock type fitting operable to allow for a syringe to attach to the housing. In yet still a further embodiment, the second inlet engages with a removable cap provided to seal the second inlet when not in use.

The present disclosure provides for a kit having component parts capable of being assembled comprising: (a) a tubular housing adapted to be sealably mounted on an elongate element of an endoscope for examining the trachea of the patient and configured to mount an adapter for an endotracheal tube for intubating the patient along and around the elongate element, the housing having at least one inlet into a cavity inside the housing for supplying at least a first fluid and an outlet for delivering the first fluid between the elongate element and an inside wall of the endotracheal tube; (b) tubing attached to the inlet port; and (c) a connector on the tube for connecting to the source of the fluid. In a further embodiment of an exemplary kit, the housing defines a longitudinal axis and comprises: (i) a first portion configured and dimensioned to be mounted along and around the elongate element along the longitudinal axis and is adapted to mount the adapter for the endotracheal tube on a distal end of the housing; and (ii) a second portion integral with the first portion and extending along the longitudinal axis from a proximal end of the first portion. The second portion is adapted at the proximal end of the housing to be mounted on a holding means for securing and sealing an end of the second portion of the elongate element.

In an exemplary embodiment, a kit according to the present disclosure further comprises a stop adapted to seal the proximal end of the second portion of the housing along and around the tubular element. The second portion is tapered to form a friction fit between the second portion of the housing and the stop. In a further embodiment, the housing comprises a second inlet into the cavity of the housing adapted to allow for a second fluid to be introduced into the housing and being delivered to the endoscope through the outlet. In still a further embodiment, the kit further comprises instructions for assembly.

The present disclosure provides for an exemplary endoscope having an elongate element for supporting an endotracheal tube, which comprises a tubular housing mounted on the elongate element of the endoscope for examining the trachea of the patient and configured to mount an adapter for the endotracheal tube for intubating the patient over and around the elongate element; the housing having an inlet into a cavity inside the housing for supplying at least a first fluid and an outlet for delivering the first fluid between the elongate element and an inside wall of the endotracheal tube. In an exemplary embodiment, the tubular element further comprises a curved or curvable portion at a distal end of the elongate element. In still a further embodiment, the endoscope further comprises a gripping means for manipulating the elongate element during intubation of a patient, wherein the gripping means comprises a handgrip and a trigger operable to curve the curved or curvable portion of the elongate element.

The present disclosure provides for a method for supplying at least a first fluid to the trachea of a patient, which comprises: (a) providing an endoscope having an elongate element for supporting an endotracheal tube, with a housing adapted to be mounted on the elongate element of an endoscope for examining the trachea of the patient and which an adapter for an endotracheal tube at the proximal end of the endotracheal tube for intubating the patient around the elongate element; the housing having an inlet into a cavity inside the housing for supplying the first fluid and an outlet for delivering the first fluid between an outside wall of the elongate element and an inside wall of the endotracheal tube through the adapter; and (b) intubating the patient with the endotracheal tube mounted on the adapter using the endoscope and supplying the first fluid to the inlet and out the outlet between the elongate element and the inside wall of the endotracheal tube to the patient. In an exemplary embodiment, the first fluid supplied is oxygen. In still a further embodiment, the first fluid is supplied so as to clear secretions from the patient's airway. In still a further embodiment, the tubular housing further comprises a second inlet into the cavity of the housing for supplying a second fluid through the outlet to the trachea of a patient. In an exemplary embodiment, the second fluid is a drug. In yet a further embodiment, the second fluid is a local anesthetic.

BRIEF DESCRIPTION OF THE DRAWINGS

FIG. 2 illustrates an environmental perspective view of an endotracheal intubation device 10 inserted into an endotracheal tube E prior to use.

FIG. 3 illustrates a side cross-sectional view of the endotracheal intubation device 10 with a cover 135 removed.

FIG. 3A is a cross-sectional view of an endotracheal tube stop 75.

FIG. 4 illustrates a distal end view of the tubular element 40 taken along line 4-4 of FIG. 3.

FIG. 6 illustrates magnified view of a first embodiment of a curvable portion 70 of the tubular element 40 of FIG. 5 having wedge shaped cuts 423.

FIG. 6A illustrates the first embodiment of a curvable portion 70 without internal components for clarity.

FIG. 6B illustrates magnified view of a second embodiment of a curvable portion 70' with cuts (411, 412).

FIG. 6C illustrates an end view of the second embodiment of the curvable portion 70' taken along line 6C-6C of FIG. 6B.

FIG. 9 illustrates a perspective view of the yoke portion 155 of the device 10.

DETAILED DESCRIPTION OF THE INVENTION

Figure 1:
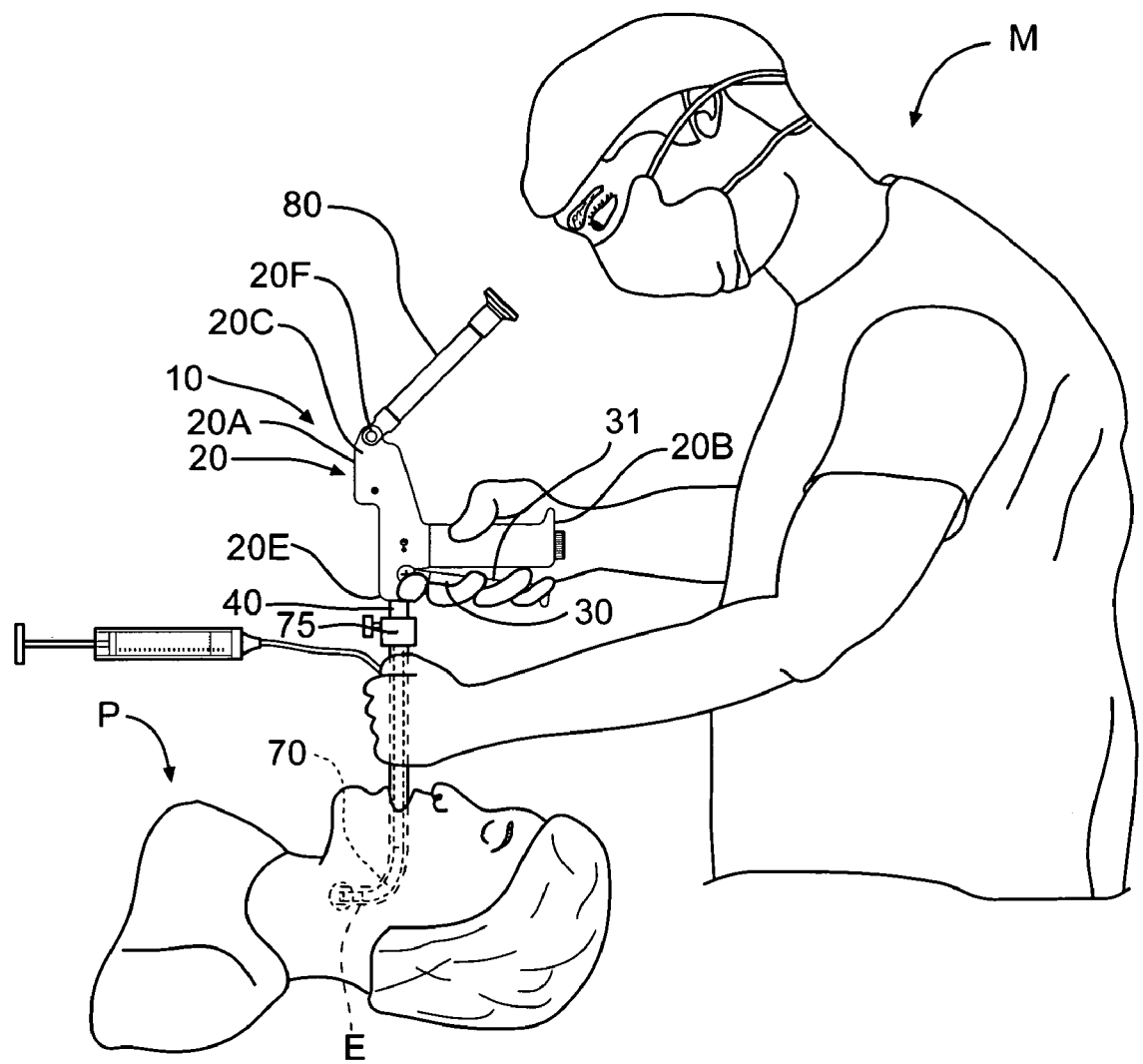
FIG. 1 illustrates an environmental perspective view of an endotracheal intubation device 10 according to the present invention in use.

All patents, patent applications, government publications, government regulations, and literature references cited in this specification are hereby incorporated herein by reference in their entirety. In case of conflict, the present description, including definitions, will control.

The term "proximal" as used herein refers to a direction towards a medical professional when the endotracheal intubation device is in use.

The term "distal" as used herein refers to a direction towards a patient who is to be endotracheally intubated when the endotracheal intubation device is in use.

The term "above" or "top" as used herein refers to a direction or side, respectively of the device corresponding to the top side of the handgrip.

The term "below" or "bottom" as used herein refers to a direction or side, respectively, of the device corresponding to the bottom side of the handgrip.

The term "left" as used herein refers to a side of the device corresponding to the left side of the handgrip.

The term "right" as used herein refers to a side of the device corresponding to the right side of the handgrip.

The term "control means" as used herein refers to any mechanism known in the art that a user can manipulate to control bending of the curvable portion. An example of a control means is a trigger as described herein. The term also encompasses such mechanism as buttons, knobs, wheels or the like that can be squeezed, turned, pressed or otherwise manipulated by a user.

The term "curvable portion" as used herein refers to a part of the tubular element which is curvable. In some embodiments, the curvable portion is provided as a portion with cuts (as slits, wedges etc.) as in the two alternate embodiments described herein.

The term "means for moving the curvable portion" as used herein encompasses any mechanism, including mechanical or electromechanical mechanisms that can transduce movement of the control means to movement of the curvable portion. The term encompasses mechanisms such as a control wire, but is not limited thereto.

The term "display means" as used herein refers to any mechanism or device for displaying an image of the throat of the patient at the distal end of the tubular element during the endotracheal intubation procedure. An example of a display means includes, but is not limited to, a liquid crystal display or other type of video display or one or more lenses which collect an image from a fiber optics system.

The term "gripping means" as used herein refers to any grip such as, but not limited to a pistol type handgrip described herein, that can be gripped by a user to hold the endotracheal intubation device.

The term "insufflation" as used herein refers to blowing a gas, liquid or powder material into an airway of a patient.

The term "pulley means" as used herein refers to any apparatus known in the art for translating force which comprises one or more pulleys.

The term "recess" as used herein is a broad term including any indentation, cleft or cut in the tubular element. The term encompasses "cuts" including narrow cuts as "slits" and also wide V-shaped cuts as "wedges" in the tubular element. "Slits" are provided as narrow cuts preferably disposed on opposed sides of the curvable portion.

The term "SMA" as used herein is an abbreviation for a shape memory alloy, also known as a memory metal or smart wire. Some examples of SMAs include, but are not limited to copper-zinc-aluminum, copper-aluminum-nickel, and nickel-titanium (NiTi) alloys such as Nitinol (Nickel Titanium Navy Ordnance Labs).

The term "tubular element" as used herein refers to an elongate member, including but not limited to a tubular element described herein. The tubular element can be cylindrical, however it is not limited thereto. Any elongate shape that an endotracheal tube can slide over is encompassed by the present invention.

The term "transmission means" as used herein refers to a any mechanism or device for transmitting an image of the throat from the viewing means to the display means. An example of a transmission means includes, but is not limited to, electrical wiring lines, fiber optic lines, and/or optical lenses.

The term "viewing means" as used herein refers to any mechanism or device for collecting an image of the throat of the patient at the distal end of the tubular element during the endotracheal intubation procedure. An example of a viewing means includes, but is not limited to, a small video camera or a lens for a fiber optics system.

U.S. patent application Ser. No. 11/230,392 to Schwartz et al., hereby incorporated herein by reference in its entirety, describes an endotracheal intubation device. The present invention is an improvement of this device. The present invention provides a device to facilitate endotracheal intubation of a patient, comprising: (a) a gripping means; (b) a tubular element having a proximal end attached to the gripping means and a distal end; (c) a curvable portion of the tubular element disposed adjacent to the distal end of the tubular element, having one or more recesses in the tubular element adapted to curve the curvable portion; (d) a control means provided on or adjacent to the gripping means; and (e) a means for moving the curvable portion transmitting force applied by the user on the control means to curve the curvable portion, wherein when the control portion is manipulated by the user the curvable portion curves into a generally curved configuration in a controlled manner from a fully straight configuration and returns to a less curved conformation when the control means is released.

Figure 7:
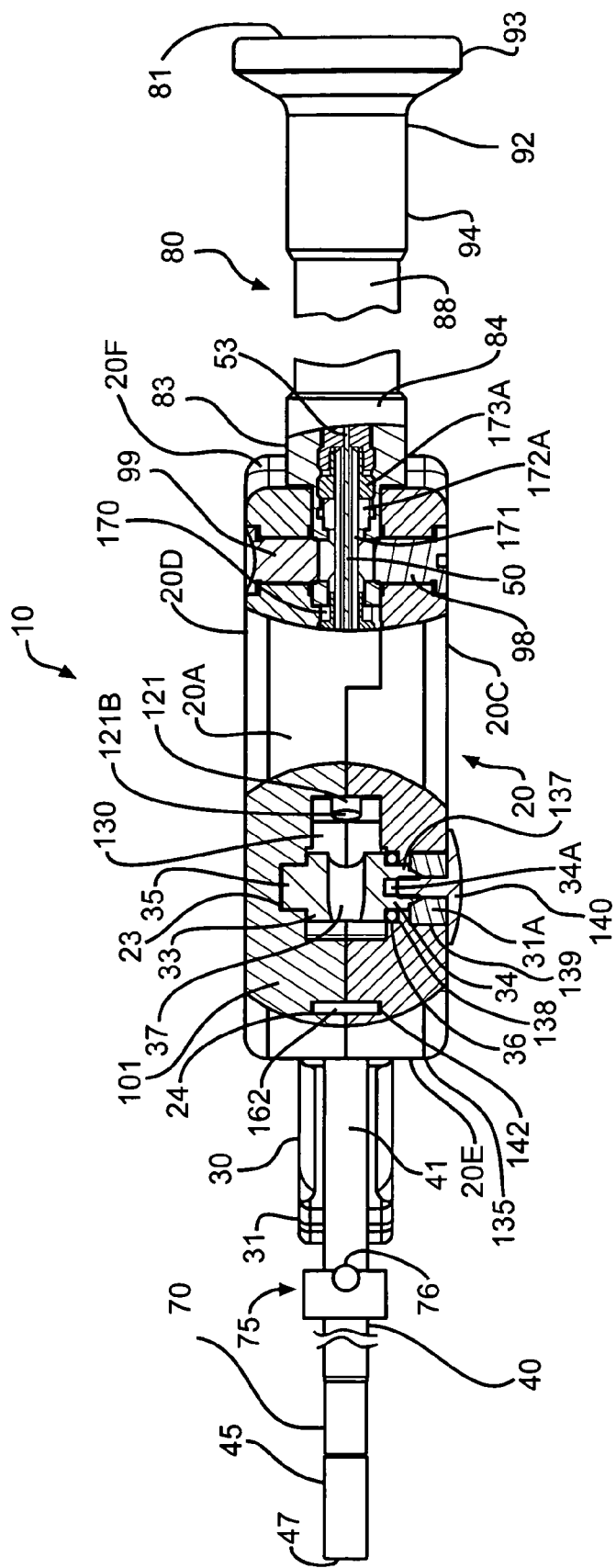
FIG. 7 illustrates a top cross-sectional view of the endotracheal intubation device 10 taken along line 7-7 of FIG. 3.
Figure 8:
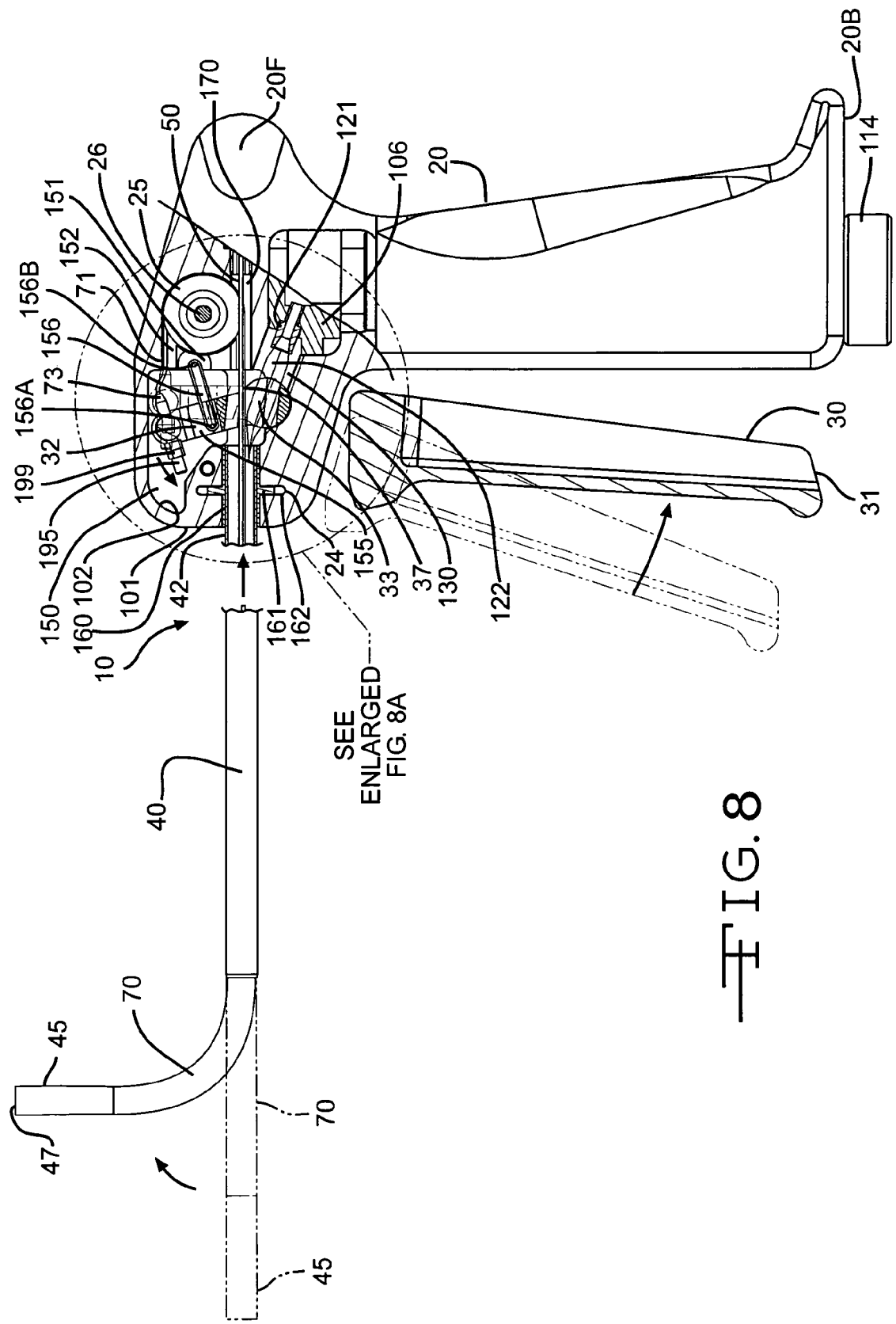
FIG. 8 illustrates a partial cross-sectional view of the endotracheal intubation device 10 of FIG. 2.

One embodiment of the present invention is illustrated in FIG. 1 through FIG. 9. This embodiment of the endotracheal intubation device 10 is illustrated in use in FIG. 1 and FIG. 2. FIG. 1 shows how a tubular element 40 of the endotracheal intubation device 10 can be inserted into a patient P by a medical practitioner M. The endotracheal intubation device 10 is gripped by the medical professional M on a handgrip 20 having a top 20A, a bottom 20B, a left 20C, a right 20D (see FIG. 7), a front 20E and a back 20F. The fingers of the medical professional grip a trigger 30 which is pivotably mounted on the handgrip 20. The trigger 30 has a first end 31 for controlled movement when the medical professional M squeezes the trigger 30 towards the handgrip 20. As illustrated in FIG. 8 when the medical professional squeezes the first end 31 of the trigger 30 a curvable portion 70 (FIGS. 1, 2, 3, 5, 6, 7 and 8) towards the distal end of the tubular element 40 is curved into a generally curved configuration in a controlled manner from a fully straight configuration. The medical professional can thereby move the distal end 47 of the tubular element 40 to safely advance the tubular element 40 into the throat of the patient. The endotracheal intubation device 10 is well sealed so that bodily fluids cannot penetrate the device 10 and damage any internal components.

FIG. 2 illustrates how an endotracheal tube E is inserted over the tubular element 40 of the endotracheal intubation device 10 to a stop 75 (FIGS. 1, 2, and 3A) prior to using the device 10 to endotracheally intubate the patient. The tubular element 40 attaches at a proximal end 42 (FIGS. 2, 3, 5, 8 and 8A) of a proximal portion 41 (FIG. 2) of the tubular element 40 at the front 20E of the handgrip 20 and extends to a distal end 47 of a distal portion 45 (FIG. 2) which is inserted into the patient's throat to place the endotracheal tube E in the patient.

A pivotable optics portion 80 is attached to the back 20F of the handgrip 20 on an eyepiece swivel 84 (see FIG. 3) at the distal end 83 of the optics portion 80. An eyepiece tube 88 projects from a proximal end 85 (FIG. 5) of the eyepiece swivel 84. At the proximal end 82 (FIG. 3) of the optics portion is an eyepiece housing 92 which is mounted over the proximal end 89 of the eyepiece tube 88. The medical practitioner M can look into the proximal end 82 of the optics portion 80 to view an image of the patient's throat as the distal end of the tubular element 40 is advanced to place the endotracheal tube E in the trachea of the patient P. Since the endotracheal intubation device 10 incorporates internal optics, it can be used in situations where an external imaging device, such as a nasopharyngoscope, is not readily available.

Figure 5:
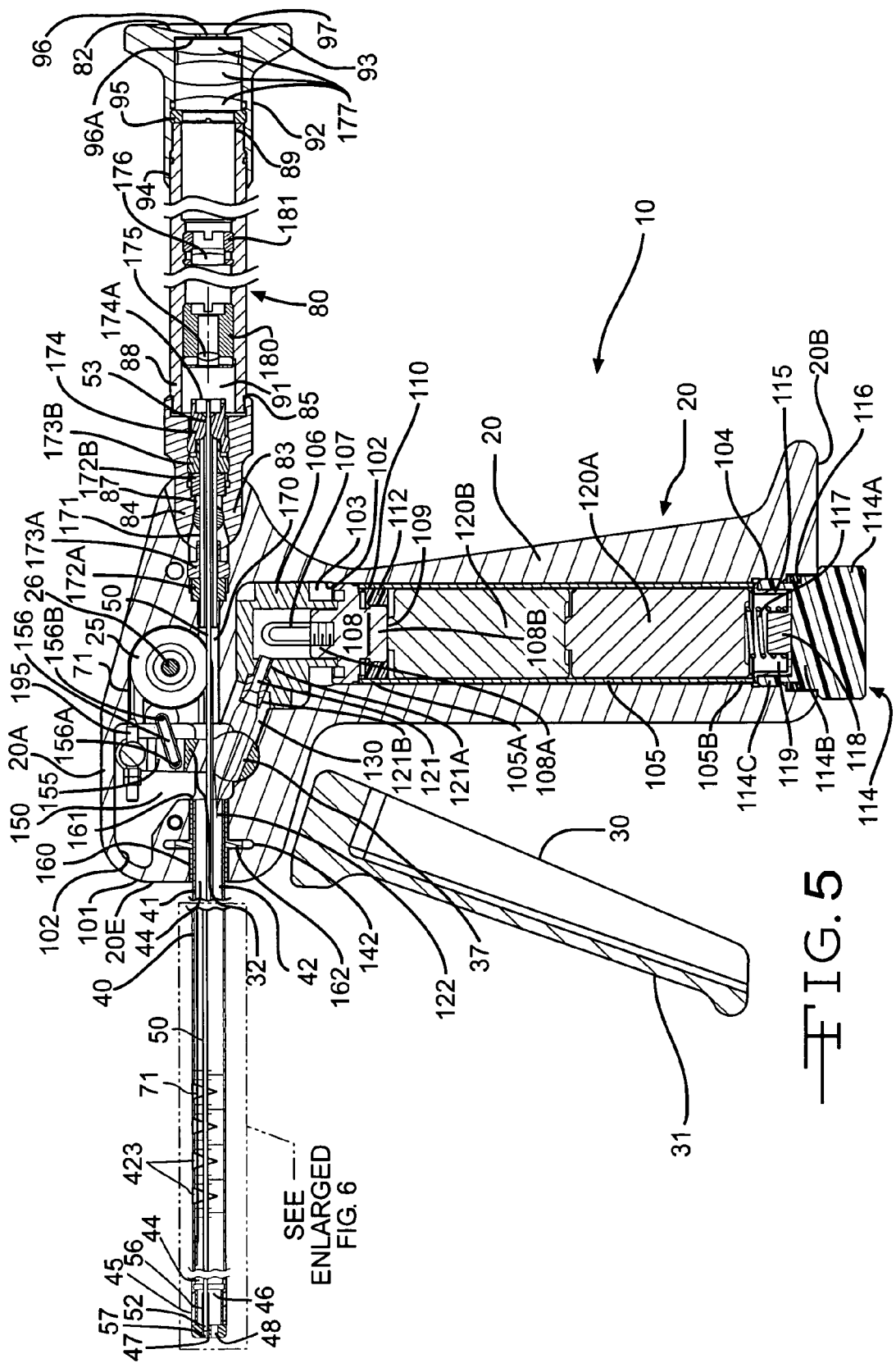
FIG. 5 illustrates a cross-sectional view of the endotracheal intubation device 10 taken along line 5-5 of FIG. 2.

FIG. 3 through FIG. 9 illustrate the internal workings of the endotracheal intubation device 10 in detail. As illustrated in FIG. 5, the handgrip 20 provides a housing 101 having an inner wall 102 which defines a lighting cavity 103 towards the bottom of the device 10. The lighting cavity 103 encloses a cylindrical battery sleeve 105 constructed of brass or other conducting material, having a top end 105A and a bottom end 105B. The battery sleeve 105 (FIG. 5) is disposed against an inner wall 102 of the housing 101 towards the bottom 20B of the handgrip 20. Two batteries 120A, 120B are arranged in series within the battery sleeve 105 in the lighting cavity 103 of the handgrip 20. The two batteries 120A, 120B are held in the lighting cavity 103 by a battery plug 114 mounted below the two batteries 120A, 120B at the bottom 20B of the handgrip 20. The battery plug 114 has a first portion 114A which can be gripped when inserting the battery plug 114 into the lighting cavity 103 after insertion of the two batteries 120A, 120B. A battery plug o-ring 116 surrounds a second portion 114B in the center of the battery plug 114 and rests snugly against the inner wall 102 of the housing 101 of the handgrip 20 when the battery plug 114 is inserted. The battery plug 114 has a third portion 114C with a thread 115 which is screwed into a threaded portion 104 in the inner wall 102 of the lighting cavity 103. Since the battery plug o-ring 116 fits snugly against the inner wall 102, the battery plug 114 will not loosen when the device 10 is in use. The battery plug o-ring 116 also keeps fluid out of the device 10.

A contact cap 119 fits into a depression in the third portion 114C of the battery plug 114. When the battery plug 114 is threaded into the handgrip 20, a spring 117 which is disposed over a projection 118 in the contact cap 119 is held against a negative terminal of a first battery 120A to make electrical contact and support the two batteries 120A, 120B in the lighting cavity 103. Enclosed above the battery sleeve 105 in the lighting cavity 103 towards the top 20A of the handgrip 20 is a lamp housing 106 (FIG. 5). Within the lamp housing 106 is a lamp 107 which is the light source for the endotracheal intubation device 10. The lamp 107 can be a xenon lamp or other similar light source. The lamp 107 is affixed to a first end 108A of a lamp base 108. The lamp housing 106 surrounds the first end 108A of the lamp base 108 to enclose the lamp 107. The second end 108B of the lamp base 108 rests in the top end 105A of the battery sleeve 105. At the second end 108B of the lamp base 108 is a first electrical contact 109 which is surrounded with an insulator ring 112. The insulator ring 112 secures the lamp base 108 in the battery sleeve 105 while also isolating the first contact 109 from electrical connection with the battery sleeve 105. A second contact 110 on the lamp base 108 extends above the insulator ring 112 and makes electrical contact with the battery sleeve 105.

Figure 8A:
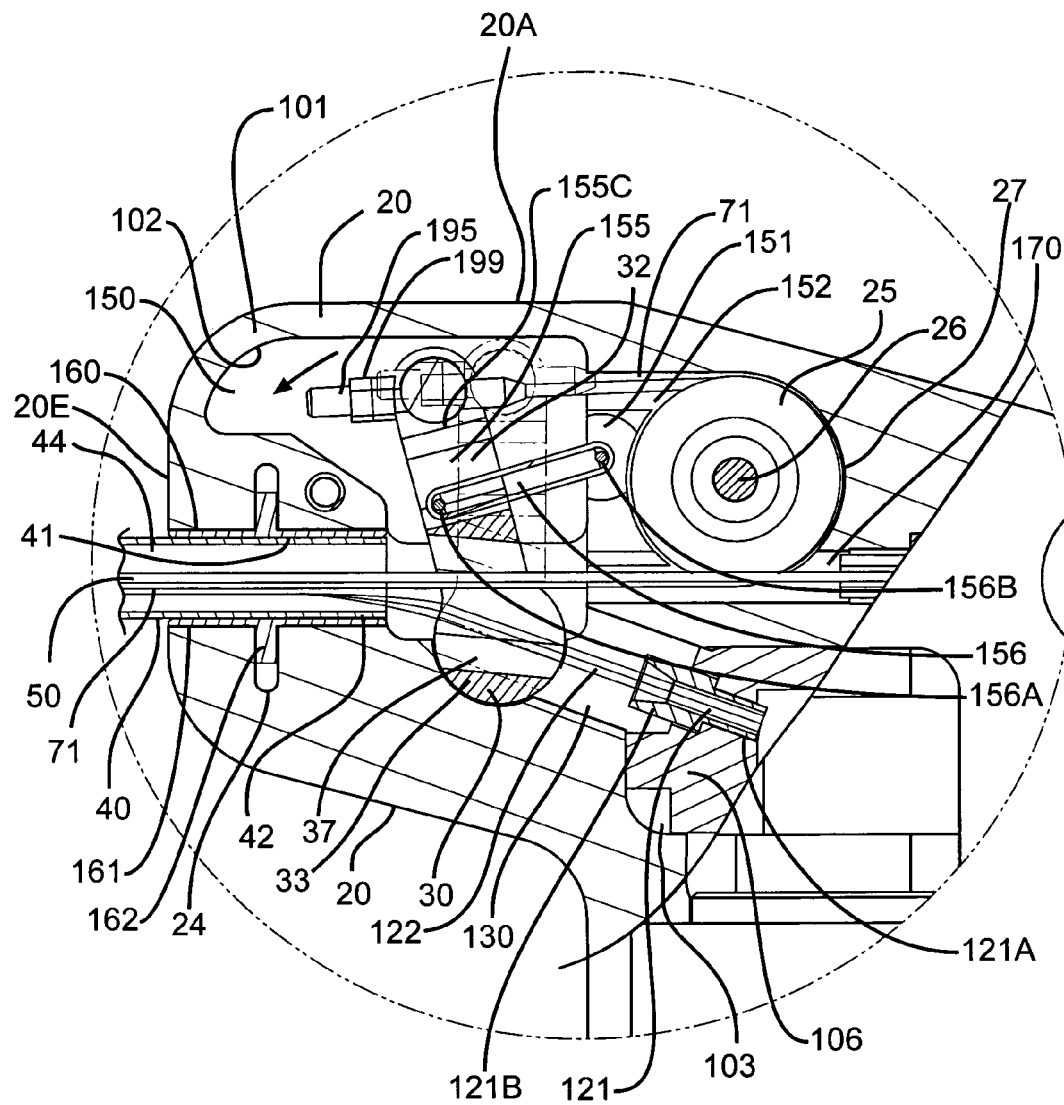
FIG. 8A illustrates a magnified cross-sectional view of the handgrip of FIG. 5.

As illustrated in FIG. 5 and FIG. 8A, the lamp housing 106 is penetrated above towards the top 20A and front 20E of the handgrip 20 by a fiber ferrule 121 into which the proximal ends of three illumination fibers 122 (FIG. 8A) are secured. The illumination fibers 122 (FIG. 8A) are held by the fiber ferrule 121 in close proximity to the lamp 107 (FIG. 5), so that the illumination fibers 122 can collect the light from the lamp 107 when it is powered by the two batteries 120A, 120B. In use, the lamp 107 can be activated by turning the battery plug 114 (FIG. 5) so as to advance the battery plug 114 into the lighting cavity 103 until the contact cap 119 makes electrical contact with the bottom end 105B of the battery sleeve 105. This action completes an electrical circuit so as to supply power to the lamp 107. The lamp 107, when supplied with power, emits light into a first end 121A (FIG. 8A) of the fiber ferrule 121, where the light is collected by the proximal ends of the three illumination fibers 122. The second end 121B (FIG. 8A) of the fiber ferrule 121 protrudes out from the lamp housing 106 and into a connecting cavity 130 (FIGS. 3, 5, 7, 8 and 8A) defined by the inner wall 102 of the housing 101 on the right and a cover 135 (FIG. 7) on the left. The connecting cavity 130 extends from the lighting cavity 103 into a lever cavity 150 (FIGS. 3, 5, 8 and 8A) which is above and distal to the lighting cavity 103. In the housing 101, adjacent to the lamp 107, is a transparent window 21 as seen in FIG. 2. The transparent window 21 is mounted in an opening that penetrates the left side 20C of the handgrip 20 and the lamp housing 106 over the lamp 107. When the lamp 107 is turned on the transparent window 21 is lit as a reminder that the power is on.

The lever cavity 150 is enclosed by the housing 101 on the right side and the cover 135 (FIG. 7) on the left side. The cover 135 is attached to the housing 101 by a front screw 136 (FIG. 2 and FIG. 3) at a front of the cover 135 and a left pivot screw 98 (FIG. 2) at a back of the cover 135. As described previously, the trigger 30 which is mounted on the handgrip 20 has a first end 31 for controlling the degree of bend of the curvable portion 70 of the tubular element 40 when the trigger 30 is squeezed towards the handgrip 20. As illustrated in FIG. 7, the first end 31 (FIG. 2) of the trigger 30 is mounted to a pivot portion 33 of the second end 32 (FIG. 3) of the trigger 30 mounted within the housing 101 at an intersection of the connecting cavity 130 (FIGS. 3, 5, 7, 8 and 8A) and the lever cavity 150 (FIGS. 3, 5, 8 and 8A). As seen in FIG. 7, the pivot portion 33 of the trigger 30 extends laterally left to right across the handgrip 20. The pivot portion 33 extends from a left mounting post 34 which is rotatably mounted in a left mounting hole 137 in the cover at the left side of the handgrip 20, to a right mounting post 35 rotatably mounted in a right mounting hole 23 in the inner wall at the right side 20D of the handgrip 20. As seen in FIG. 7, a pivot o-ring 36 fits around the left mounting post 34 between the pivot portion 33 and rests in a groove 138 surrounding the left mounting hole 137. A hinge portion 31A on the first end 31 of the trigger 30 is mounted in a trigger mounting hole 139 in the cover 135 which extends through the cover 135 to the left mounting hole 137. A trigger pivot pin 140 penetrates a first pivot pin hole 141 through the hinge portion 31A of the first end 31 of the trigger 30 and a second pivot pin hole 34A in the left mounting post 34 of the pivot portion 33 to secure the first end 31 of the trigger 30 to the pivot portion 33. An elongate yoke portion 155, seen in FIG. 8A, of the second end 32 of the trigger 30 extends above the pivot portion 33 into the lever cavity 150 of the handgrip 20. Between the pivot portion 33 and the yoke portion 155, a pivot channel 37 extends through the second end 32 of the trigger 30 from front to back which provides access between the lighting cavity 103 and the lever cavity 150.

As illustrated in FIG. 8A, a mounting channel 160 (FIGS. 5, 8 and 8A) extends a length through the housing 101 and the cover 135 (FIG. 7) of the handgrip 20. The mounting channel 160 extends from the front side of the handgrip 20 to the bottom of the lever cavity 150 adjacent to the pivot channel 37 in the second end 32 of the trigger 30. Mounted flush with the wall defining the mounting channel 160 and extending the length of the mounting channel 160 is a tubular mounting shaft 161. The mounting shaft 161 is anchored in the handgrip 20 by means of a central rim 162 (FIG. 8 and FIG. 8A) which encircles the mounting shaft 161 and fits into a slot 24 (FIG. 7, FIG. 8 and FIG. 8A) in the handgrip 20 and a slot 142 in the cover 135 (FIG. 7) to enclose the central rim 162. The proximal end 42 (FIG. 8A) of the proximal portion 41 of the tubular element 40 has an internal radius such that it fits tightly within the tubular mounting shaft 161. The tubular element 40 extends through the length of the mounting shaft 161 to secure the tubular element 40 to the handgrip 20.

Externally, an adjustable endotracheal tube stop 75 as shown in FIG. 3 and FIG. 3A encircles the proximal portion 41 of the tubular element 40. The endotracheal tube stop 75 has a first end 75A (FIG. 3A) having a first circular opening 75C with a diameter adapted to receive an end of a standard adapter 77 on an endotracheal tube E as illustrated in FIG. 3A. The endotracheal tube stop 75 grips the standard adapter 77 at the end of the endotracheal tube in the first opening 75C, so that it will not slide off during the intubation procedure. At a second end 75B of the endotracheal tube stop 75 is a second opening 75D having a diameter fits over the tubular element 40. The endotracheal tube stop 75 is secured in place on the proximal portion 41 by means of a stop screw 76.

Figure 3B:
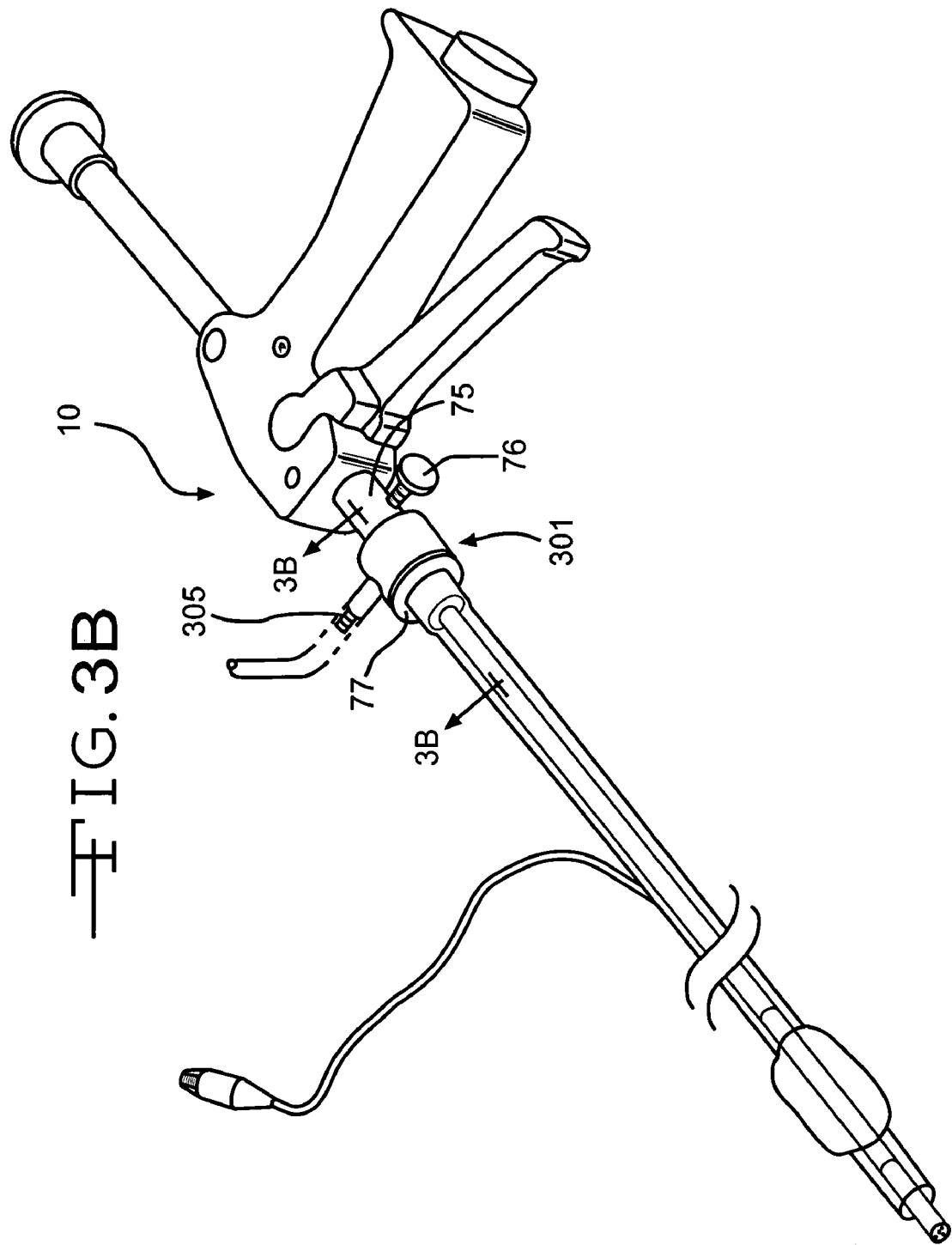
FIG. 3B illustrates an environmental perspective view of an endotracheal intubation device 10 having an insufflation attachment 301.
Figure 3C:
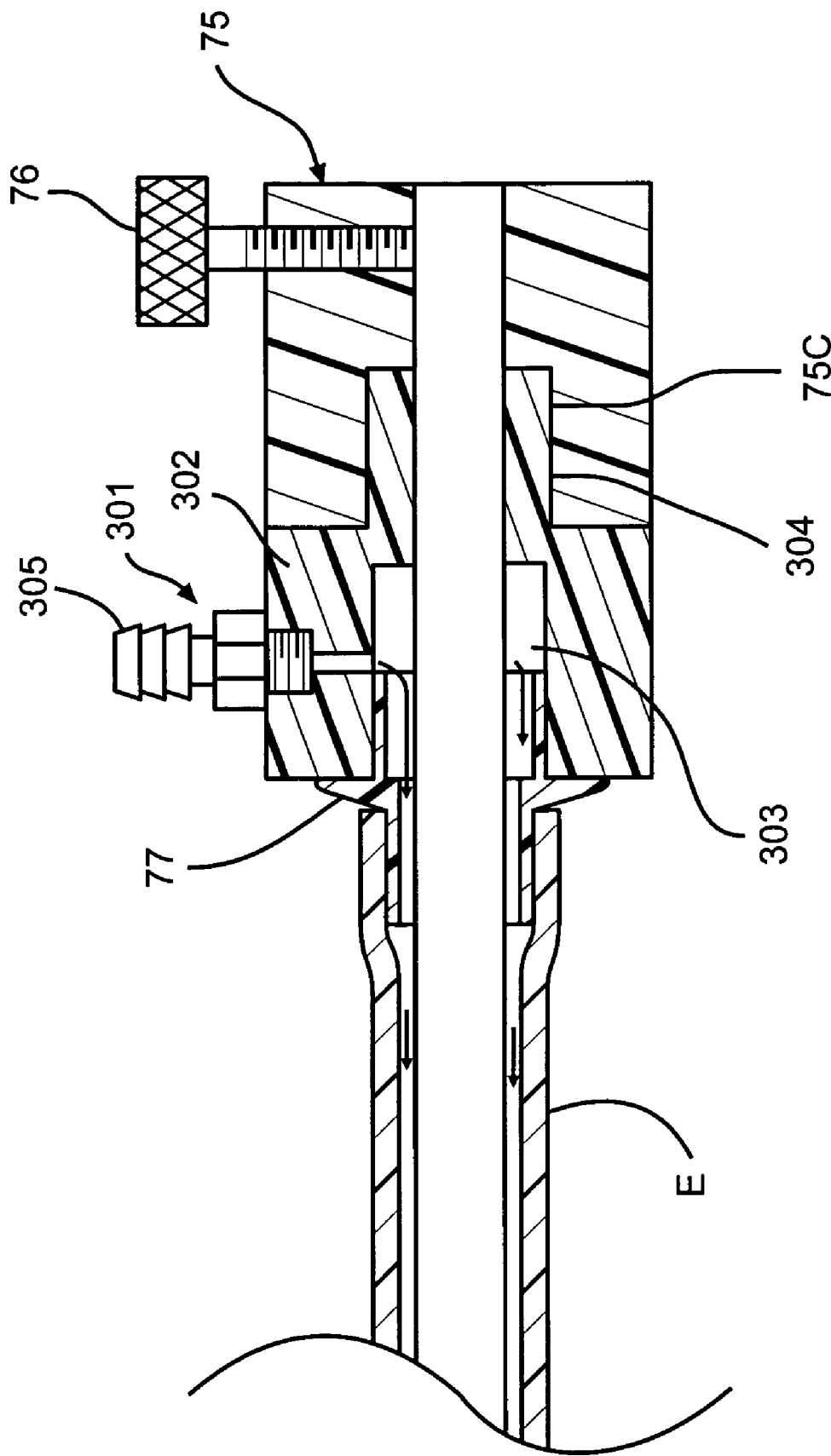
FIG. 3C is a cross-sectional view of an endotracheal tube stop 75 with an insufflation attachment 301.
Figure 3D:
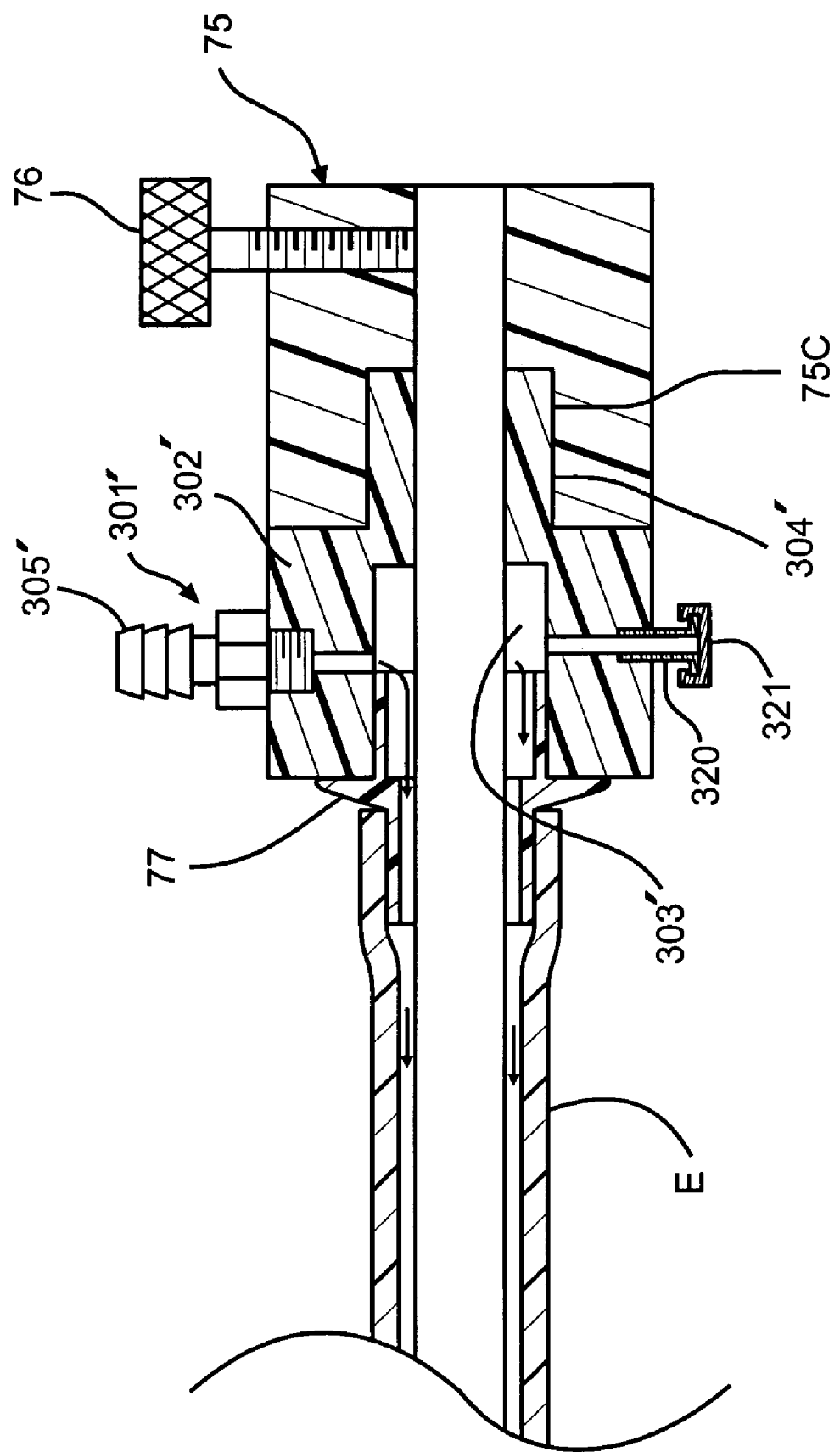
FIG. 3D is a cross-sectional view of an endotracheal tube stop 75 with another embodiment of a insufflation attachment 301' having a liquid port 320.

Alternatively, as illustrated in FIGS. 3B, 3C and 3D, an insufflation attachment (301, 301') can be inserted between the standard adapter 77 and the endotracheal tube stop 75. A wide portion (302, 302') of the insufflation attachment (301, 301') has a cavity (303, 303') into which the standard adapter 77 fits. At an opposing end of the insufflation attachment (301, 301') a narrow portion (304, 304') projects from the wide portion (302, 302') having an outer diameter that fits into the first opening 75C at the first end 75A of the endotracheal tube stop 75 and an inner diameter that fits over the tubular element 40. In some embodiments, the insufflation attachment (301, 301') is disposable. The insufflation attachment (301, 301') can be hooked up to an oxygen source tubing placed by means of a port (305, 305') passing through the wide portion (302, 302') and into the cavity (303, 303') to allow oxygen to flow into and through the endotracheal tube E to clear secretions from the patient's airway and supply oxygenation. Optionally, in one embodiment of the insufflation attachment 301', as illustrated in FIG. 3D, a liquid port 320 can be added as well to allow injection of a local anesthetic drug. A drug, for example an aminoester or aminoamide local anesthetic such as lidocaine can be administered through the liquid port 320 so that it passes down the endotracheal tube E and into the patient. In some embodiments the liquid port 320 is provided as a luer-lock type attachment so that a syringe (not shown) can be easily attached to the insufflation attachment 301'. A removable cap 321 is provided to seal the liquid port 320 when not in use.

An internal channel 44 (FIG. 8A) in the tubular element 40 extends the length of the tubular element 40 from the proximal end 42 which opens into the lever cavity 150 adjacent to the pivot channel 37, through the proximal portion 41 of the tubular element 40, the curvable portion 70 (FIGS. 1, 2, 3, 5, 6, 7 and 8), and through the distal portion 45 to the distal end 47 (FIG. 6) of the tubular element 40 where a distal head 48 is inserted to cap the internal channel at distal end 47. The three illumination fibers 122 (FIG. 8A) carry light from the lamp 107 collected at the proximal ends in the fiber ferrule 121 in the lamp housing 106 adjacent to the lamp 107. The three illumination fibers 122 extend through the connecting cavity 130, the pivot channel 37, the lever cavity 150 and into the proximal end 42 of the internal channel 44, where they extend to the distal end 47 of the distal portion 45 of the tubular element 40 and through the distal head 48 where they terminate at the distal ends 122B, 123B, 124B as illustrated in FIG. 4. When the battery plug 114 is turned to complete the circuit and provide power to the lamp 107, the throat of the patient is illuminated with light from the distal ends 122B, 123B, 124B of the three illumination fibers 122.

Figure 10:
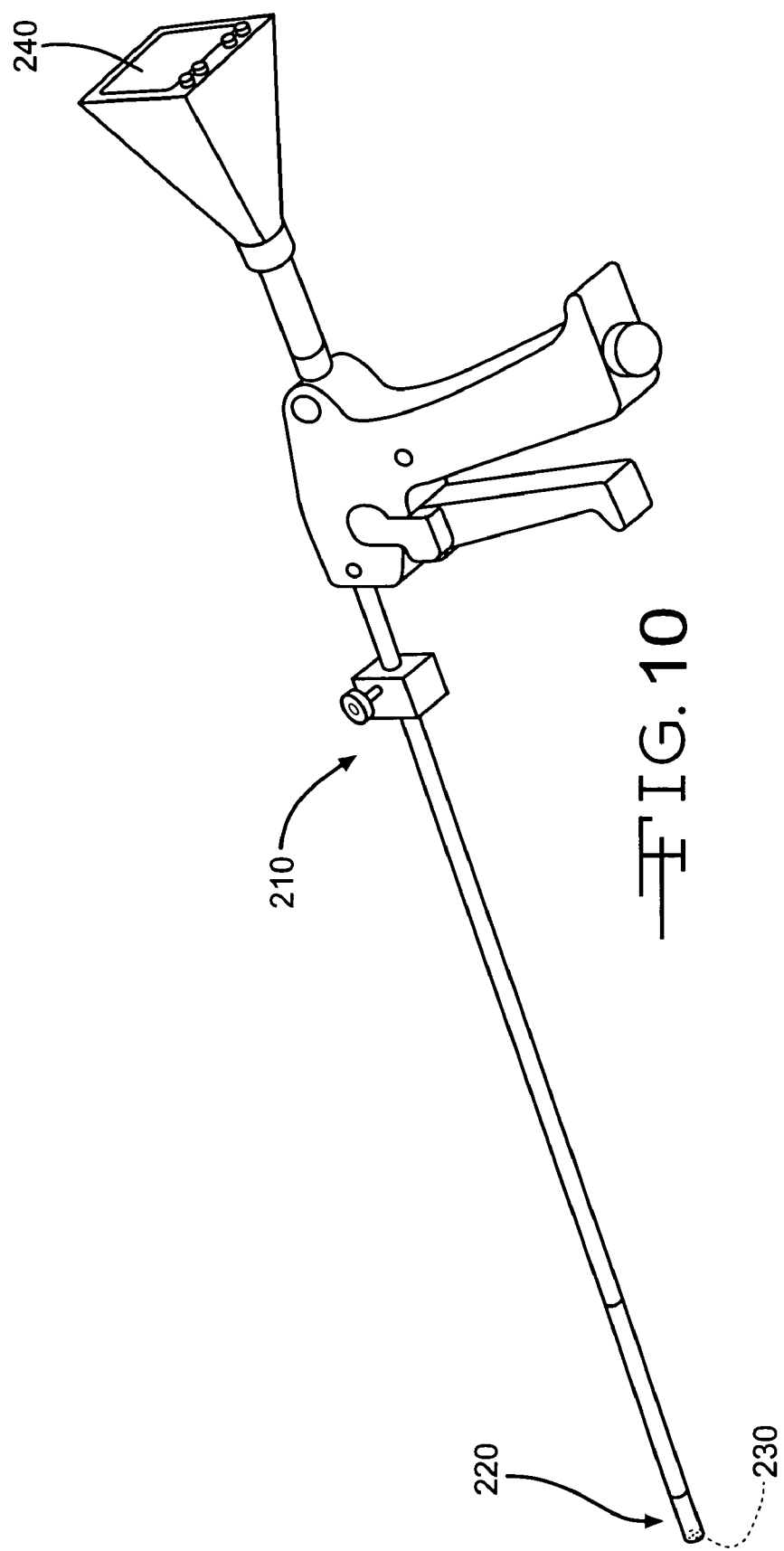
FIG. 10 illustrates a perspective view of an alternate embodiment an endotracheal intubation device 210 according to the present invention having a video system.
Figure 11:
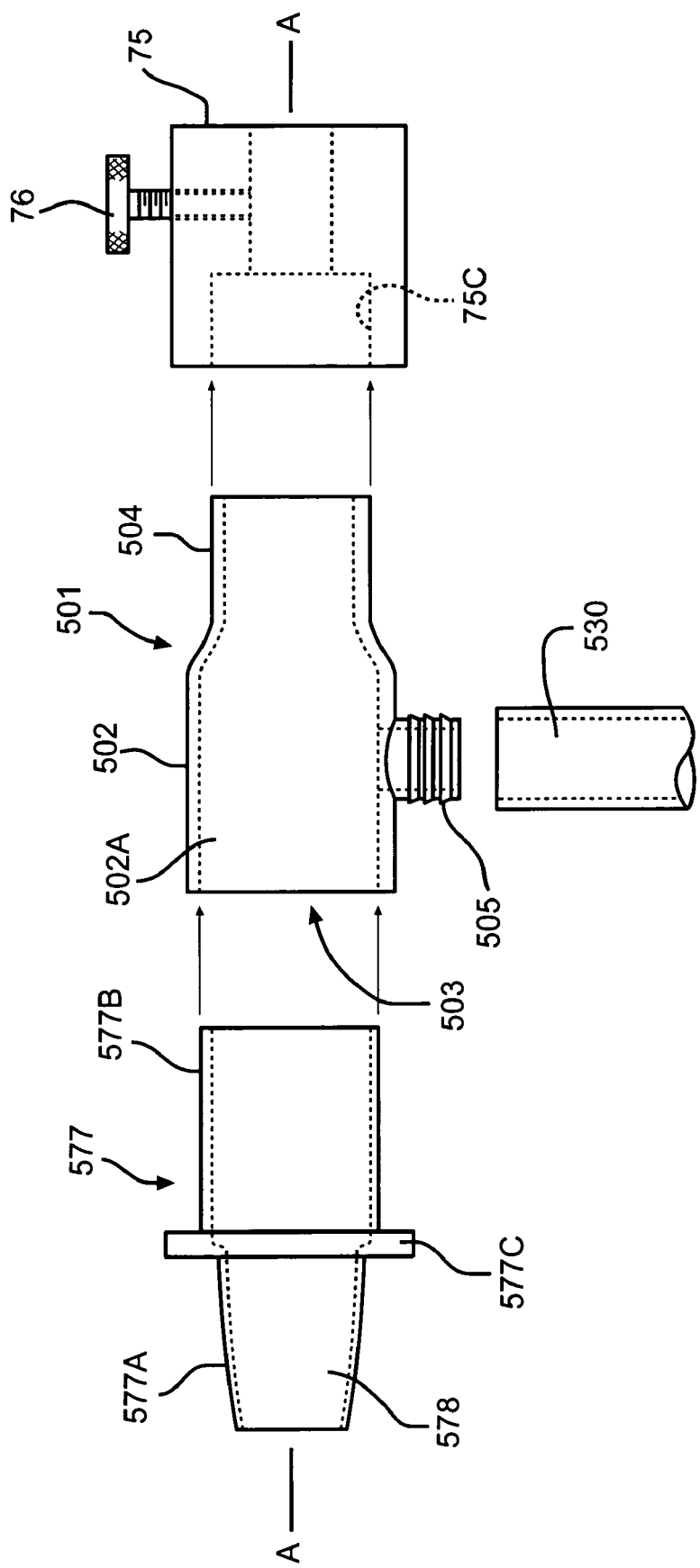
FIG. 11 is an exploded side view of an exemplary device for facilitating fluid delivery to the trachea of a patient.
Figure 12:
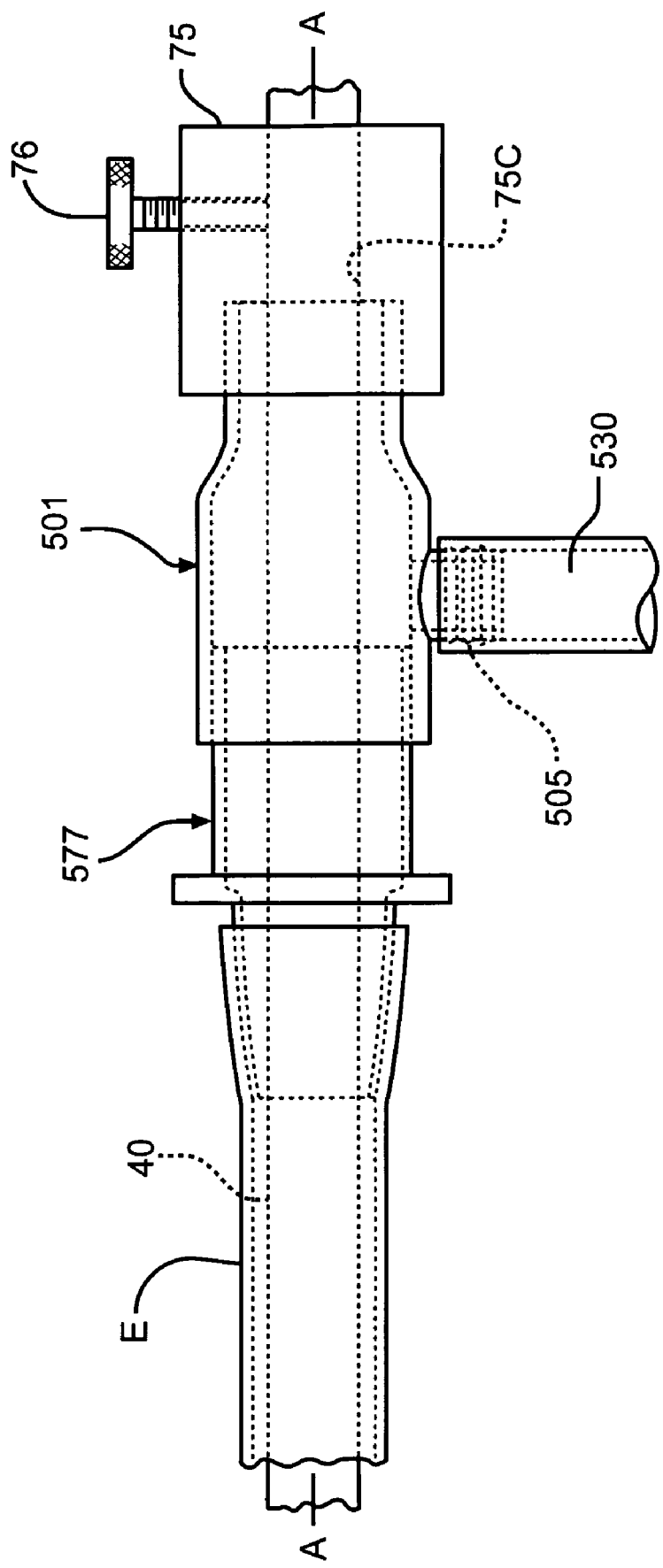
FIG. 12 is an assembled view of the exemplary device of FIG. 11 with an endotracheal tube mounted thereon.
Figure 13:
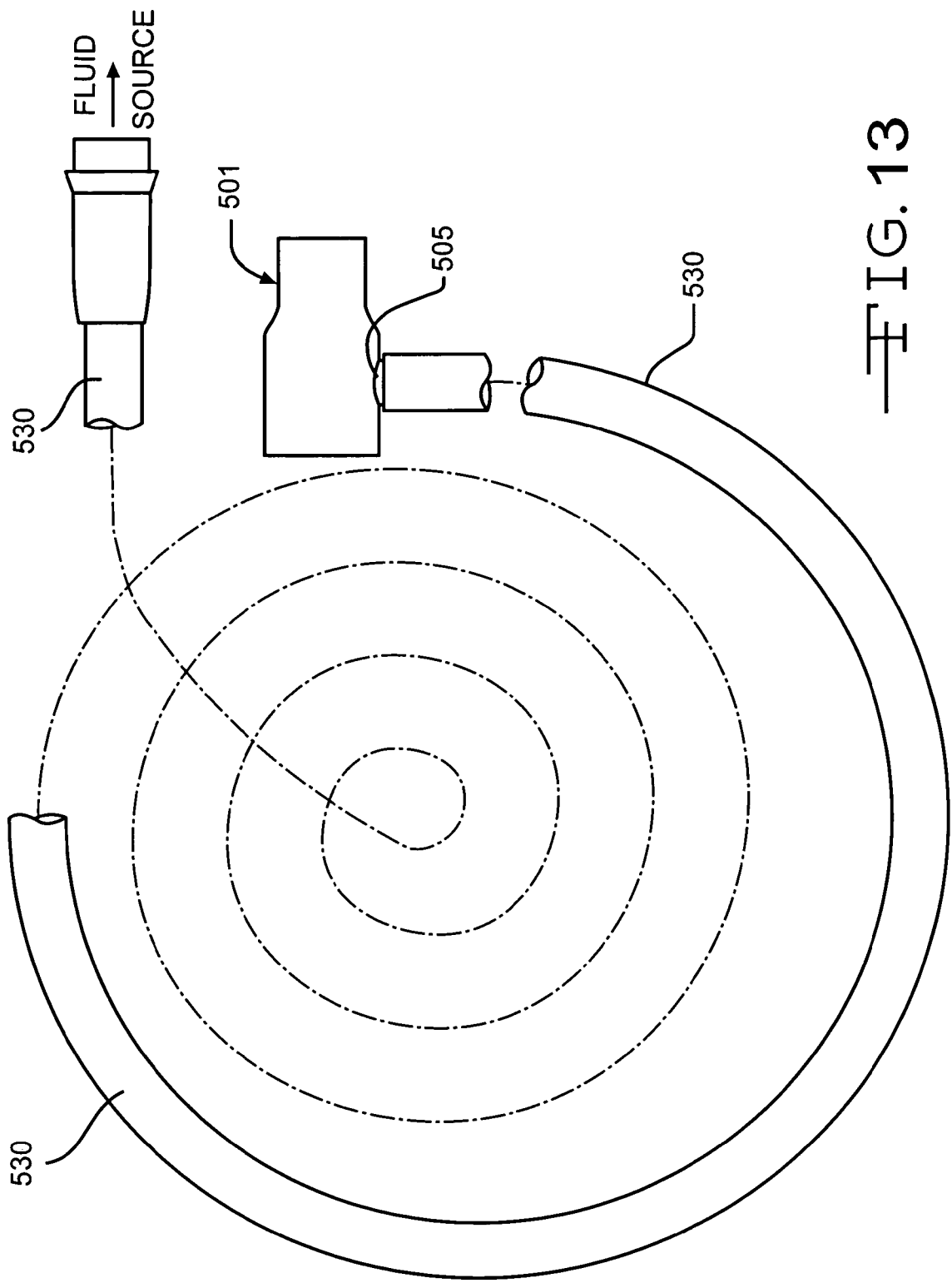
FIG. 13 illustrates the exemplary device from FIG. 11 further comprising a tube for the delivery of the fluid.
Figure 14:
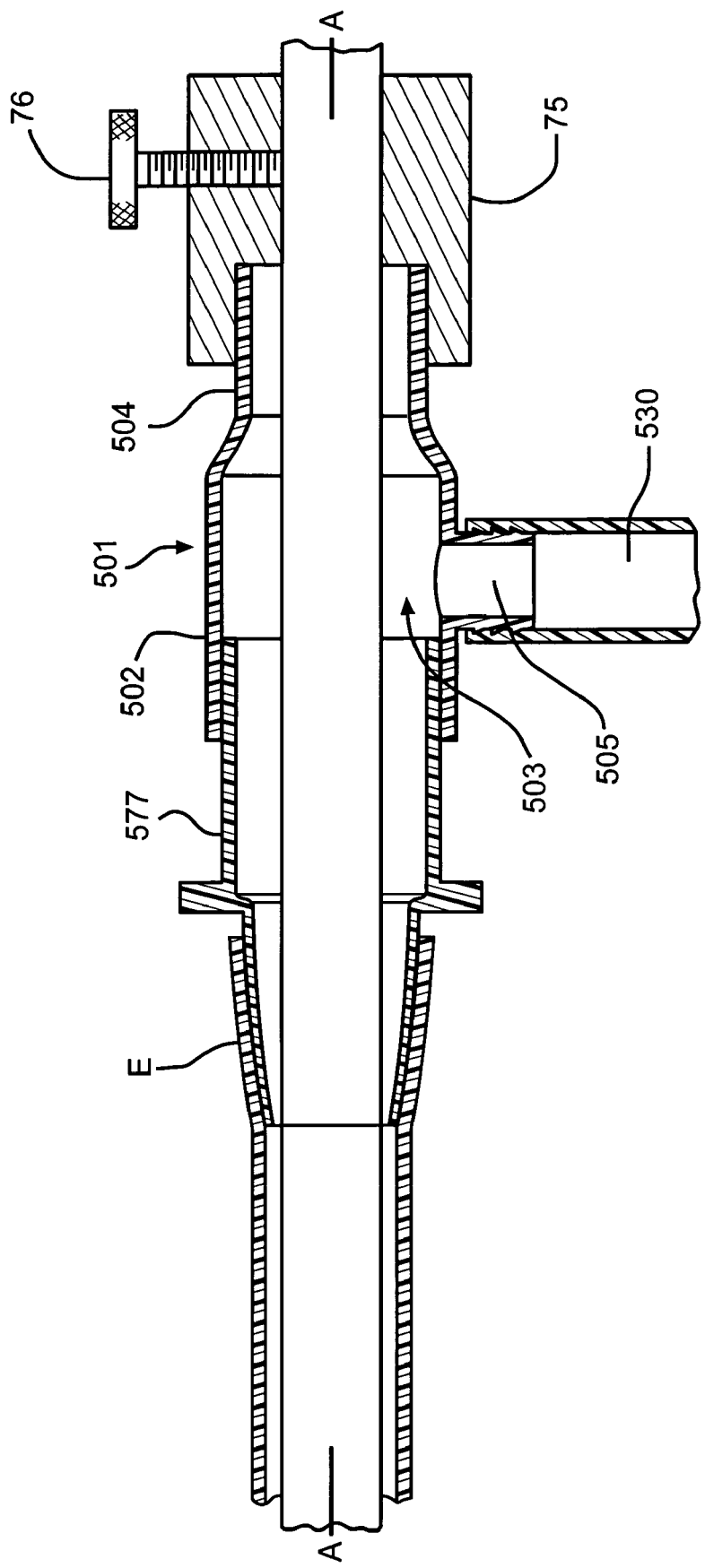
FIG. 14 is a cross sectional side view of the device of FIG. 11 mounted on an elongate element of an endoscope.

As best seen in FIG. 6, the distal head 48 inserts into the distal end 47 of the distal portion 45 of the tubular element 40. A tube 56 (FIG. 6) extends from the distal head 48 inside of the distal portion 45 to support a first end 52 of the optics fiber 50. As illustrated in FIG. 4, a lens 57 for the optics fiber 50 is located between the distal ends 122B, 123B, 124B of the three illumination fibers 122. In one embodiment, the lens 57 in the aperture has approximately a 60° field of view. The optics fiber 50 extends from the lens 57 (FIG. 4, FIG. 5 and FIG. 6) at a first end 52 (FIG. 5 and FIG. 6) of the optics fiber 50 and passes through the length of the internal channel 44 (FIG. 5, FIG. 6 and FIG. 8A) to a second end 53 (FIG. 5 and FIG. 7) at the back of handgrip 20. The optics fiber 50 extends from the internal channel 44 (FIG. 5, FIG. 6 and FIG. 8A) of the tubular element 40, into the lever cavity 150 (FIG. 3, FIG. 5 and FIG. 8A), through the pivot channel 37 (FIG. 5, FIG. 7, FIG. 8, FIG. 8A and FIG. 9) and into an optics channel 170 (FIG. 3, FIG. 5, FIG. 7, FIG. 8, and FIG. 8A) which penetrates the housing 101 and through to the back of the handle 20. From the back of the handle 20 the optics fiber 50 enters an internal channel 87 (FIG. 5) which passes through an eyepiece swivel 84 (FIG. 3 and FIG. 5) at the distal end 83 of the optics portion 80. The second end 53 (FIG. 5) of the optics fiber 50 passes through the internal channel 87 of the eyepiece swivel 84 and terminates at a proximal end 85 of the eyepiece swivel 84 (FIG. 3 and FIG. 5). An alternative embodiment of the present invention is shown in FIG. 10 which is identical to the embodiment of FIG. 1-FIG. 9, except for the optics system. In this embodiment, a small video camera 220 at the distal end 230 of the device 210 is wired through to a small video display 240 at the proximal end of the device 210. In some embodiments, a small video display in a proximal end of the device can be viewed through an opening in the eyepiece housing when the distal end of the tubular element is advanced forward during the endotracheal intubation procedure.

As illustrated in FIG. 2 and FIG. 5, an eyepiece tube 88 attaches to the proximal end 85 (FIG. 5) of the eyepiece swivel 84 (FIG. 5) having an internal channel 91 (FIG. 5) which extends from the eyepiece swivel 84 (FIG. 5) to the proximal end 89 of the eyepiece tube 88. A distal end 94 (FIG. 2 and FIG. 5) of an 18 mm Ortho eyepiece housing 92 (FIG. 2, FIG. 3 and FIG. 5) is threaded over the eyepiece tube 88 so that the proximal end 89 of eyepiece tube 88 rests against a lock ring 95 (FIG. 5) in the eyepiece housing 92 (FIG. 5). The proximal end 93 (FIG. 3 and FIG. 5) of the eyepiece housing 92 flares outward to provide a circular lip used as an eye rest. At the proximal end 93 of the eyepiece housing 92 is an opening 96 (FIG. 5) centrally located in a concave portion 97 (FIG. 5) of the eyepiece housing 92. The optics portion 80 focuses light collected at the lens 57 (FIG. 4 and FIG. 6) of the optics fiber 50 by means of a series of lenses 175, 176, 177 (FIG. 5) from light which is emitted from the second end 53 of the optics fiber 50. An image of the throat of the patient can be viewed through the opening 96 in the eyepiece housing 92 when the distal end 47 of the tubular element 40 is advanced forward during the endotracheal intubation procedure.

As illustrated in FIG. 5, the second end 53 of the optics fiber 50 is enclosed within a flexible tubing 171 which can be constructed of silicone. The flexible tubing 171 is supported at a distal end by a section of silicone tubing 172A surrounding the flexible tubing 171 which is held by a lock ring 173A in the back of the handgrip 20. In a similar manner, the proximal end of the flexible tubing 171 is supported in the internal channel 87 of the eyepiece swivel 84 by a section of silicone tubing 172B surrounding the flexible tubing 171 which is held by a lock ring 173B. The flexible tubing 171 encloses the optics fiber 50 extending from the optics channel 170 and through the internal channel 87 of the eyepiece swivel 84 so as to protect the optics fiber 50 when the optics portion 80 is moved. As seen in FIG. 7, the eyepiece swivel 84 is mounted at a left side on the left pivot screw 98 which penetrates the cover 135 at the back 20F and left 20C of the handgrip 20. In like fashion, the eyepiece swivel 84 is mounted at a right side on a right pivot screw 99 penetrating the housing 101 at the back 20F and right 20D of the handgrip 20. As can be seen in FIG. 7, the left pivot screw 98 and the right pivot screw 99 do not obstruct the internal channel 87 of the eyepiece swivel 84. Therefore, the optics portion 80 can be moved up and down with respect to the handgrip 20 although the flexible tubing 171 extends through to the proximal end 85 of the eyepiece swivel 84. The second end 53 of the optics fiber 50 is covered with a cover glass 174A (FIG. 5) and held by a mount 174 disposed over the distal end 171A of the flexible tubing 171.

The optics fiber 50 is held by the mount 174 so that an image is projected through the series of lenses 175, 176, 177 (FIG. 5) in the eyepiece tube 88 and the eyepiece housing 92. A distal lens 175 is mounted in a distal magnification cell 180 and a proximal lens 176 is mounted in a proximal magnification cell 181. The lenses 175, 176 mounted in the eyepiece tube project light onto lenses 177 in the eyepiece housing 92. As illustrated in FIG. 5, mounted within the eyepiece housing 92 against the opening 96 is a window 96A sealed with a gasket to protect the internal components from fluids. The lenses 177 of the eyepiece housing 92 are configured so that an image of the throat of the patient can be viewed through the opening 96 in the eyepiece housing 92.

When it is clear from the image of the throat of the patient that the distal end 47 of the tubular element 40 must be curved to avoid throat structures such as the back of the throat, the trigger 30 can be squeezed to curve the curvable portion 70 to then view the vocal cords. As can be seen in FIG. 8A, when the first end 31 of the trigger 30 is squeezed towards the handgrip 20 the pivot portion 33 and the yoke portion 155 rotate forward so as to act as a lever. A tension spring 156 is attached at a first end 156A (FIG. 8A and FIG. 9) to the yoke portion and at a second end 156B to a back wall of the lever cavity 150 (See FIG. 9). The tension spring 156 resists forward movement of the yoke portion 155, and returns the yoke portion 155 backward again when pressure on the first end 31 of the trigger 30 is released.

As illustrated in FIG. 9, a left projection 155A and a right projection 155C of the yoke portion 155 extend upwards to define a space through which a hollow cylindrical yoke swivel 190 is mounted. A hollow wire fitting 195 is mounted inside the cylindrical yoke swivel 190. A length adjacent to a second end 73 of a control wire 71 is secured inside the wire fitting 195 so that the control wire 71 extends from the second end 195B of the wire fitting 195 towards the back 20F of the handgrip 20. Two jam nuts 199 are threaded and locked over an external thread on a front end 195A of the wire fitting 195 and rest against a rim 193 at an end of the yoke swivel towards the front 20E of the handgrip 20. A left yoke pin 188 penetrates a hole 155B through the left projection 155A of the yoke 155, a left hole through the yoke swivel 190, and into a left hole in the wire fitting 195. In a similar manner, a right yoke pin 189 penetrates a hole 155D through the right projection 155C of the yoke portion 155, a right hole through the yoke swivel 190, and into a right hole in the wire fitting 195. The left yoke pin 188 and right yoke pin 189 allow the assembled pieces to swivel in the yoke portion 155 when the yoke portion 155 moves forward and backward in the level cavity 150.

The housing 101 and cover 135 of the handgrip 20 also encloses a pulley 25 (FIG. 3, FIG. 5, FIG. 8, FIG. 8A and FIG. 9) which is mounted on a pulley pin 26 (FIG. 3, FIG. 5, FIG. 8, FIG. 8A and FIG. 9) which extends from a right side mounted in the housing 101 and a left side which is mounted in the cover 135. The pulley 25 fits into a pulley cavity 27 (FIG. 8A) located behind the lever cavity 150. The control wire 71 towards the second end 73 passes through a control wire hole 152 (FIG. 8A) in the back wall 151 of the lever cavity 150 and over a top of the pulley 25 in the pulley cavity 27. The control wire 71 wraps around to a bottom of the pulley 25 where the control wire 71 enters the optics channel 170 (FIG. 8A) beneath the pulley 25 and extends forward substantially parallel to the optics fiber 50 through the pivot channel 37 (FIG. 8A, FIG. 9) and the lever cavity 150. The control wire 71 extends into the internal channel 44 of the tubular element 40 at the proximal end 42 of the proximal portion 41 and through the internal channel 44 of the tubular element 40 to a first end 72 (FIG. 6) of the control wire 71 at a distal end 70B of the curvable portion 70 as seen in FIG. 6.

A first embodiment of the curvable portion 70 is illustrated in FIG. 6. This embodiment is illustrated in FIG. 6A without internal components for clarity. A second embodiment of a curvable portion 70' is illustrated (with protective tubing 65 removed for clarity) in FIG. 6B. The endotracheal intubation device 10 is the same in these two embodiments except for the curvable portions (70, 70'). FIG. 6A and FIG. 6B do not illustrate internal components of the device to improve clarity, however it is to be understood that the illumination fibers 122, the optics fiber 50 and the control wire 71 pass through the curvable portions (70, 70'). In these embodiments, the curvable portion (70, 70') is continuous with the rest of the tubular element 40. Cuts (411, 412, 421, 422, 423) are made, optionally by means of a laser cutting device, in the tubing to allow the curvable portions (70, 70') to bend when the trigger is squeezed.

In the embodiment, illustrated in FIG. 6A, three sets (421, 422, 423) of alternating cuts are made in the curvable portion 70 of the tubular element 40. Two sets of cuts (421, 422) are made as slits on top and bottom of the curvable portion 70. A first set of cuts 421 are on a top side of the curvable portion 70, and a second set of cuts 422 are on the bottom side of the curvable portion 70. A third set of cuts 423 that are wedge (ie. "V") shaped are provided on a top side of the curvable portion 70. The length of the curvable portion 70 in this embodiment is 6.5 centimeters (2.56 inches), the length of the proximal portion 41 (see FIG. 3) of the tubular element 40 is 29 cm (11.4 inches), and the length of the distal portion 45 of the tubular element 40 is 2.5 cm (0.98 inches). The tubular element 40 is this embodiment has an outer diameter of 5.75 millimeters (0.226 inches).

In the embodiment illustrated in FIG. 6B, two sets of alternating cuts (411, 412) are made as slits in the curvable portion 70' of the tubular element 40'. A first set of cuts 411 are on a top side of the curvable portion 70', and a second set of cuts 412 are on the bottom side of the curvable portion 70'. In some embodiments, the first sets of cuts are deeper than the second set. In one embodiment, the first set of cuts 411 are of a depth α of 0.18 inches (4.57 mm) with a width of 0.015 inches (0.38 mm). In this embodiment, the second set of cuts 412 are of a depth β of 0.0675 inches (1.71 mm) with a width of 0.015 inches (0.38 mm). In this embodiment, the cut separation is 0.035 inches (0.89 mm). The length of the curvable portion 70' in this embodiment is 2.6 inches (66 mm). As seen in FIGS. 6B and C, the depth α of the first set of cuts 411 and the depth β of the second set of cuts 412 overlap such that the curvable portion 70' bends along a bend line γ at a distance θ from the top of the curvable portion 70'. In some embodiments, the distance θ is about ⅔ of the width of the tubular element 40.

The entire length of the curvable portion (70, 70') is covered with a protective tubing 65 (seen in FIG. 6A) such as Viton® tubing (DuPont, Wilmington, Del.) or other robust tubing material which seals the internal components of the curvable portion (70, 70') through which the optics fiber 50 and the three illumination fibers 122 extend. The control wire 71 extends to at or near a distal end of the curvable portion (70, 70') where the control wire is secured (not shown). As illustrated in FIG. 8 and FIG. 8A when the first end 31 of the trigger 30 is squeezed, the second end 32 of the trigger 30, acting as a lever, pulls the second end 73 of the control wire 71 around the pulley 25 so that tension is applied to the control wire 71. The tension on the control wire 71 curves along bend line γ the curvable portion (70, 70') in a controlled manner from a fully straight configuration.

While the tubular element 40 can be constructed of stainless steel, polymer or other sturdy material, in some preferred embodiments it is constructed of a shape memory alloy (SMA). Any shape memory alloy such as a copper-zinc-aluminum, copper-aluminum-nickel, and nickel-titanium (NiTi) alloys can be used, such as, but not limited to Nitinol. The tubular element 40, when constructed of a shape memory alloy such as Nitinol. The shape memory alloy (SMA) of the curvable portion (70, 70') will flex when the trigger 30 is squeezed, and then will return to its original conformation when the trigger 30 is released due to the tendency of the SMA to spring back to a less curved conformation.

Figure 15:
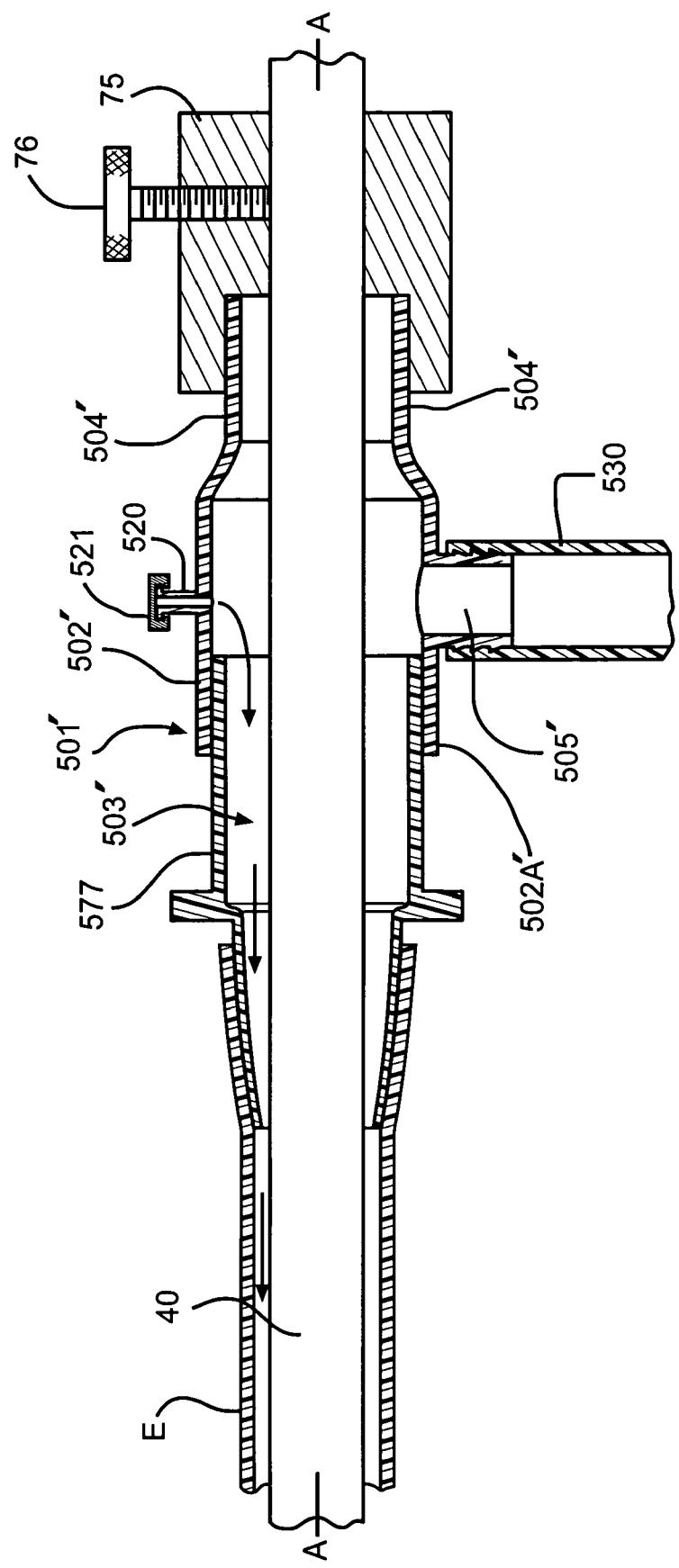
FIG. 15 is a cross sectional view of an exemplary device for facilitating fluid delivery to the trachea of a patient further comprising a second fluid inlet.

In an exemplary embodiment, the present disclosure provides for a device, as illustrated in FIGS. 11-14, for facilitating delivery of fluid to the trachea of a patient. FIG. 15 illustrates a device comprising similar features as device of FIGS. 11-14 further comprising a second inlet 521 for additional fluid delivery. The device as shown in FIGS. 11-15 comprises a tubular housing 501, 501' defining a longitudinal axis A-A and is operable to be mounted on an elongate member 40 of an exemplary endoscope. Housing 501, 501' is operable as an insufflation device similar to insufflation device 301, 301' described in FIGS. 3C and 3D. Exemplary housing 501 can be inserted between an adapter 577 and a holding means such as endotracheal tube stop 75. A first portion (502, 502') of the device (501, 501') defines a cavity (503, 503') into which the adapter 577 fits. At an opposing end of housing (501, 501') a second portion (504, 504') projects from the first portion (502, 502') having an outer diameter that fits into a first opening 75C of a holding means for securing and sealing an end of the second portion (504, 504') to elongate element 40 at a first end 75A of the holding means. Typically the holding means is an endotracheal tube stop 75. In an exemplary embodiment, the second portion (504, 504') can be fabricated to define a smaller diameter than the first portion (502, 502'). The second portion (504, 504') typically defines an inner diameter adapted to fit over the tubular element 40. Thus, in an exemplary embodiment, tubular housing (501, 501') is sealably mounted on elongate element 40. In an exemplary embodiment, the second portion (504, 504') is tapered towards the proximal end to allow for a friction fit with tube stop 75.

In an exemplary embodiment, tubular housing (501, 501') is disposable. Housing (501, 501') comprises an inlet (505, 505') on the first portion (502, 502'). The inlet (505, 505') extends from an outer surface (502A, 502A') of the first portion (502, 502') into the cavity (503, 503'). Adapter 577 is adapted to allow for an endotracheal tube E to be mounted over and around elongate element 40. In an exemplary embodiment, adapter 577 is removable and comprises a first section 577A and a second section 577B. First section 577A can be tapered to securely be mounted over and around tubular element 40 and further support the mounting of endotracheal tube E. Second section 577B is sized and shaped to be mounted within cavity 503 of the first portion (502A, 502A') of housing (501, 501'). Typically, adapter 577 is mounted within housing (501, 501') along the defined longitudinal axis A-A. The first section 577A is typically at the distal end of adapter 577 and the second section 577B is at the proximal end. In an exemplary embodiment, adapter 577 further comprises an outwardly extending flange member 577C around an outer surface 578 of adapter 577 to allow for a friction fit to form between the adapter and the first portion (502, 502') of housing 501, 501'). The adapter 577 can be fabricated from a plastic material in an exemplary embodiment the first section 577A is integrally formed with flange 577C and second section 577B.

Housing (501, 501') can be hooked up to a fluid source tubing 530 placed by means of the inlet (505, 505'). Thus, the tubing 530 mounted on at least a first inlet (505, 505') allows for a fluid from the fluid source to pass through the first portion (502, 502') of the housing (501, 501') and into the cavity (503, 503') to allow oxygen to flow into and through an endotracheal tube E. Endotracheal tube E can be mounted on a distal end of adapter 577. When mounted, endotracheal tube E defines a fluid passageway between an inner surface of the endotracheal tube E and the elongate tubular member 40. In an exemplary embodiment, the fluid source is an oxygen source. Oxygen can be delivered through tubing 530 to the trachea of the patient through device 501, 501'. In an exemplary embodiment, the fluid delivered to the trachea of the patient is operable to clear secretions from the patient's airway and supply oxygenation.

Optionally, in an exemplary embodiment as shown with respect to FIG. 15, device 501' further comprises a second inlet 520. In an exemplary embodiment, second inlet 520 can be a liquid inlet adapted to allow injection of a local anesthetic drug. A drug, for example an aminoester or aminoamide local anesthetic such as lidocaine can be administered through the exemplary inlet 520 so that it passes down the endotracheal tube E and into the patient. In an exemplary embodiment, inlet 505 and 520 are characterized as ports. In a further exemplary embodiment, second inlet 520 is provided as a luer-lock type attachment so that a syringe (not shown) can be easily attached to the device 501'. A removable cap 521 is provided to seal the second inlet 520 when not in use.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. A device for facilitating fluid delivery to the trachea of a patient, which comprises:
   (a) a tubular housing adapted to be sealably mounted on an elongate element of an endoscope for examining the trachea of the patient and configured to mount an adapter for an endotracheal tube for intubating the patient over and around the elongate element, the housing having at least one inlet into a cavity inside the housing for supplying at least a first fluid and an outlet for delivering the first fluid between the elongate element and an inside wall of the endotracheal tube mounted on the adapter.

2. The device of claim 1, wherein the housing defines a longitudinal axis and comprises a first portion configured and dimensioned to be mounted along and around the elongate element along the longitudinal axis and is adapted to mount an adapter for the endotracheal tube on a distal end of the housing and a second portion integral with the first portion and extending along the longitudinal axis from a proximal end of the first portion, wherein the second portion is adapted at the proximal end of the housing to be mounted on a holding means for securing and sealing an end of the second portion of the elongate element.

3. The device of claim 2, wherein the inlet extends from an outside surface of the first portion into the cavity and the outlet extends from the cavity inside the housing.

4. The device of claim 3, wherein the housing is adapted to support a removable adapter mounted on the first portion extending along the longitudinal axis at the distal end of the housing adapted to allow for the endotracheal tube to be sealably mounted along and around the elongate element along the longitudinal axis.

5. The device of claim 4, wherein the adapter defines an opening extending from a first section to a second section, wherein the opening is sized and shaped to allow the adapter to be mounted along and around the elongate element and the second section is sized and shaped to allow the adapter to be sealably and removably mounted within an opening in the first portion of the housing.

6. The device of claim 5, wherein the adapter comprises an outwardly extending flange member around an outer surface of the adapter to allow a friction fit to form between the adapter and the first portion of the housing.

7. The device of claim 2, wherein the holding means is a endotracheal tube stop mounted on a proximal end of the tubular element and adapted to form a seal between the second portion and the elongate element and wherein the second portion is tapered to allow for a friction fit to form between the second portion and the stop.

8. The device of claim 1, wherein the at least inlet is a port connected to a fluid delivery tube for supplying the fluid to the housing.

9. The device of claim 8, wherein the fluid delivery tube is fabricated from a plastic material.

10. The device of claim 1, wherein the housing is fabricated from a plastic material and is disposable after use with a single patient.

11. The device of claim 1, further comprising a second inlet into the cavity of the housing adapted to allow for introducing a second fluid through the outlet to reach the trachea of a patient.

12. The device of claim 11, wherein the second inlet has a luer-lock type fitting operable to allow for a syringe to attach to the housing.

13. The device of claim 12, further comprising a removable cap provided to seal the second inlet when not in use.

14. A kit having component parts capable of being assembled comprising:
   (a) a tubular housing adapted to be sealably mounted on an elongate element of an endoscope for examining the trachea of the patient and configured to mount an adapter for an endotracheal tube for intubating the patient along and around the elongate element, the housing having at least one inlet into a cavity inside the housing for supplying at least a first fluid and an outlet for delivering the first fluid between the elongate element and an inside wall of the endotracheal tube;
   (b) tubing attached to the inlet port; and
   (c) a connector on the tube for connecting to the source of the fluid.

15. The kit according to claim 14, wherein the housing defines a longitudinal axis and comprises a first portion configured and dimensioned to be mounted along and around the elongate element along the longitudinal axis and is adapted to mount the adapter for the endotracheal tube on a distal end of the housing and a second portion integral with the first portion and extending along the longitudinal axis from a proximal end of the first portion, wherein the second portion is adapted at the proximal end of the housing to be mounted on a holding means for securing and sealing an end of the second portion of the elongate element.

16. The kit according to claim 14, further comprising a stop adapted to seal the proximal end of the second portion of the housing along and around the tubular element, wherein the second portion is tapered to form a friction fit between the second portion of the housing and the stop.

17. The kit according to claim 14, wherein the tubular housing further comprises a second inlet into the cavity of the housing adapted to allow for a second fluid to be introduced into the housing and being delivered to the endoscope through the outlet.

18. The kit according to claim 14, further comprising instructions for assembly.

19. An endoscope having an elongate element for supporting an endotracheal tube, which comprises:
   (a) a tubular housing mounted on the elongate element of the endoscope for examining the trachea of the patient and configured to mount an adapter for the endotracheal tube for intubating the patient over and around the elongate element, the housing having an inlet into a cavity inside the housing for supplying at least a first fluid and an outlet for delivering the first fluid between the elongate element and an inside wall of the endotracheal tube.

20. The endoscope of claim 19, wherein the tubular element further comprises a curved or curvable portion at a distal end of the elongate element.

21. The endoscope of claim 20, further comprising a gripping means for manipulating the elongate element during intubation of a patient, wherein the gripping means comprises a handgrip and a trigger operable to curve the curved or curvable portion of the elongate element.

22. A method for supplying at least a first fluid to the trachea of a patient, which comprises:
   (a) providing an endoscope having an elongate element for supporting an endotracheal tube, with a housing adapted to be mounted on the elongate element of an endoscope for examining the trachea of the patient and which an adapter for an endotracheal tube at the proximal end of the endotracheal tube for intubating the patient around the elongate element, the housing having an inlet into a cavity inside the housing for supplying the first fluid and an outlet for delivering the first fluid between an outside wall of the elongate element and an inside wall of the endotracheal tube through the adapter; and (b) intubating the patient with the endotracheal tube mounted on the adapter using the endoscope and supplying the first fluid to the inlet and out the outlet between the elongate element and the inside wall of the endotracheal tube to the patient.

23. The method of claim 22, wherein the first fluid supplied is oxygen.

24. The method of claim 22, wherein the first fluid is supplied so as to clear secretions from the patient's airway.

25. The method of claim 22, wherein the tubular housing further comprises a second inlet into the cavity of the housing for supplying a second fluid through the outlet to the trachea of a patient.

26. The device of claim 25, wherein the second fluid is a drug.

27. The device of claim 25, wherein the second fluid is a local anesthetic.

* * * * *